(12) United States Patent
Jenson et al.

(10) Patent No.: US 8,002,824 B2
(45) Date of Patent: Aug. 23, 2011

(54) CARDIAC VALVE, SYSTEM, AND METHOD

(75) Inventors: Mark L. Jenson, Greenfield, MN (US); William J. Drasler, Minnetonka, MN (US); Daniel M. Lafontaine, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/508,369

(22) Filed: Jul. 23, 2009

(65) Prior Publication Data

US 2009/0287298 A1    Nov. 19, 2009

Related U.S. Application Data

(63) Continuation of application No. 10/933,088, filed on Sep. 2, 2004, now Pat. No. 7,566,343.

(51) Int. Cl.
*A61F 2/24* (2006.01)

(52) U.S. Cl. ..................................... 623/2.12

(58) Field of Classification Search ................. 623/1.24, 623/1.26, 2.38, 2.12, 2.13–2.19
See application file for complete search history.

(56) References Cited

U.S. PATENT DOCUMENTS

| | | | |
|---|---|---|---|
| 3,671,979 A | 6/1972 | Moulopoulos | 3/1 |
| 4,291,420 A | 9/1981 | Reul | 3/1.5 |
| 4,787,901 A | 11/1988 | Baykut | 623/2 |
| 4,872,874 A | 10/1989 | Taheri | 623/1 |
| 4,935,030 A | 6/1990 | Alonso | 623/2 |
| 4,994,077 A | 2/1991 | Dobben | 623/2 |
| 5,002,567 A | 3/1991 | Bona et al. | 623/2 |
| 5,141,491 A | 8/1992 | Bowald | 604/22 |
| 5,163,953 A | 11/1992 | Vince | 623/2 |
| 5,219,355 A | 6/1993 | Parodi et al. | 606/191 |
| 5,254,127 A | 10/1993 | Wholey et al. | 606/153 |
| 5,327,774 A | 7/1994 | Nguyen et al. | 73/37 |
| 5,332,402 A | 7/1994 | Teitelbaum | 623/2 |
| 5,370,685 A | 12/1994 | Stevens | 623/2 |
| 5,411,552 A | 5/1995 | Anderson et al. | 623/2 |
| 5,469,868 A | 11/1995 | Reger | 128/898 |
| 5,480,423 A | 1/1996 | Ravenscroft et al. | 623/1 |
| 5,500,014 A | 3/1996 | Quijano et al. | 623/2 |
| 5,545,214 A | 8/1996 | Stevens | 623/2 |
| 5,554,185 A | 9/1996 | Block et al. | 623/2 |
| 5,643,208 A | 7/1997 | Parodi | 604/96 |
| 5,693,087 A | 12/1997 | Parodi | 623/1 |
| 5,713,953 A | 2/1998 | Vallana et al. | 623/2 |
| 5,716,370 A | 2/1998 | Williamson, IV et al. | 606/153 |
| 5,735,859 A | 4/1998 | Fischell et al. | 606/108 |
| 5,741,326 A | 4/1998 | Solovay | 623/1 |
| 5,741,333 A | 4/1998 | Frid | 623/12 |
| 5,800,506 A | 9/1998 | Perouse | 623/1 |
| 5,824,061 A | 10/1998 | Quijano et al. | 623/2 |
| 5,879,320 A | 3/1999 | Cazenave | 604/8 |
| 5,895,419 A | 4/1999 | Tweden et al. | 623/2 |
| 5,910,170 A | 6/1999 | Reimink et al. | 623/2 |
| 6,010,531 A | 1/2000 | Donlon et al. | 623/2 |

(Continued)

FOREIGN PATENT DOCUMENTS

EP    0 380 666    8/1990

(Continued)

*Primary Examiner* — Bruce E Snow

(74) *Attorney, Agent, or Firm* — Vidas, Arrett & Steinkraus

(57) ABSTRACT

A cardiac valve with a support frame having a first end member and a second end member opposing the first end member in a substantially fixed distance relationship, and a cover extending over the support frame to allow for unidirectional flow of a liquid through the valve.

10 Claims, 11 Drawing Sheets

U.S. PATENT DOCUMENTS

| | | | | |
|---|---|---|---|---|
| 6,042,607 | A | 3/2000 | Williamson, IV et al. | 623/2 |
| 6,139,575 | A | 10/2000 | Shu et al. | 623/2.12 |
| 6,287,334 | B1 | 9/2001 | Moll et al. | 623/1.24 |
| 6,312,447 | B1 | 11/2001 | Grimes | 606/219 |
| 6,355,030 | B1 | 3/2002 | Aldrich et al. | 606/28 |
| 6,402,780 | B2 | 6/2002 | Williamson, IV et al. | 623/2.11 |
| 6,419,696 | B1 | 7/2002 | Ortiz et al. | 623/2.37 |
| 6,425,916 | B1 | 7/2002 | Garrison et al. | 623/2.11 |
| 6,440,164 | B1 | 8/2002 | DiMatteo et al. | 623/1.24 |
| 6,451,054 | B1 | 9/2002 | Stevens | 623/2.11 |
| 6,454,799 | B1 | 9/2002 | Schreck | 623/2.18 |
| 6,461,366 | B1 | 10/2002 | Seguin | 606/144 |
| 6,503,272 | B2 | 1/2003 | Duerig et al. | 623/1.24 |
| 6,508,833 | B2 | 1/2003 | Pavcnik et al. | 623/1.15 |
| 6,564,805 | B2 | 5/2003 | Garrison et al. | 128/898 |
| 6,569,196 | B1 | 5/2003 | Vesely | 623/2.14 |
| 6,602,286 | B1 | 8/2003 | Strecker | 623/1.24 |
| 6,629,534 | B1 | 10/2003 | St. Goar et al. | 128/898 |
| 6,635,085 | B1 | 10/2003 | Caffey et al. | 623/2.1 |
| 6,666,885 | B2 | 12/2003 | Moe | 623/2.12 |
| 6,666,886 | B1 | 12/2003 | Tranquillo et al. | 623/2.42 |
| 6,669,725 | B2 | 12/2003 | Scott | 623/2.36 |
| 6,673,109 | B2 | 1/2004 | Cox | 623/2.12 |
| 6,676,698 | B2 | 1/2004 | McGuckin, Jr. et al. | 623/1.24 |
| 6,676,702 | B2 | 1/2004 | Mathis | 623/2.36 |
| 6,682,558 | B2 | 1/2004 | Tu et al. | 623/2.11 |
| 6,682,559 | B2 | 1/2004 | Myers et al. | 623/2.13 |
| 6,685,739 | B2 | 2/2004 | DiMatteo et al. | 623/1.24 |
| 6,692,512 | B2 | 2/2004 | Jang | 606/200 |
| 6,695,866 | B1 | 2/2004 | Kuehn et al. | 606/213 |
| 6,695,878 | B2 | 2/2004 | McGuckin, Jr. et al. | 623/1.19 |
| 6,709,456 | B2 | 3/2004 | Langberg et al. | 623/2.37 |
| 6,709,457 | B1 | 3/2004 | Otte et al. | 623/2.4 |
| 6,716,241 | B2 | 4/2004 | Wilder et al. | 623/1.24 |
| 6,716,244 | B2 | 4/2004 | Klaco | 623/2.4 |
| 6,719,767 | B1 | 4/2004 | Kimblad | 606/151 |
| 6,719,784 | B2 | 4/2004 | Henderson | 623/1.44 |
| 6,719,786 | B2 | 4/2004 | Ryan et al. | 623/2.11 |
| 6,719,787 | B2 | 4/2004 | Cox | 623/2.12 |
| 6,719,788 | B2 | 4/2004 | Cox | 623/2.12 |
| 6,719,789 | B2 | 4/2004 | Cox | 623/2.13 |
| 6,719,790 | B2 | 4/2004 | Brendzel et al. | 623/2.4 |
| 6,723,038 | B1 | 4/2004 | Schroeder et al. | 600/16 |
| 6,723,122 | B2 | 4/2004 | Yang et al. | 623/2.1 |
| 6,723,123 | B1 | 4/2004 | Kazatchkov et al. | 623/2.2 |
| 6,726,715 | B2 | 4/2004 | Sutherland | 623/2.1 |
| 6,726,716 | B2 | 4/2004 | Marquez | 623/2.36 |
| 6,726,717 | B2 | 4/2004 | Alfieri et al. | 623/2.36 |
| 6,730,118 | B2 | 5/2004 | Spenser et al. | 623/1.24 |
| 6,730,121 | B2 | 5/2004 | Ortiz et al. | 623/2.17 |
| 6,730,122 | B1 | 5/2004 | Pan et al. | 623/2.33 |
| 6,736,845 | B2 | 5/2004 | Marquez et al. | 623/2.11 |
| 6,736,846 | B2 | 5/2004 | Cox | 623/2.12 |
| 6,749,630 | B2 | 6/2004 | McCarthy et al. | 623/2.36 |
| 6,752,813 | B2 | 6/2004 | Goldfarb et al. | 606/139 |
| 6,752,828 | B2 | 6/2004 | Thornton | 623/1.24 |
| 6,755,857 | B2 | 6/2004 | Peterson et al. | 623/2.17 |
| 6,761,734 | B2 | 7/2004 | Suhr | 623/1.35 |
| 6,761,735 | B2 | 7/2004 | Eberhardt et al. | 623/2.1 |
| 6,764,494 | B2 | 7/2004 | Menz et al. | 606/159 |
| 6,764,508 | B1 | 7/2004 | Roehe et al. | 623/2.11 |
| 6,764,509 | B2 | 7/2004 | Chinn et al. | 623/2.12 |
| 6,764,510 | B2 | 7/2004 | Vidlund et al. | 623/2.34 |
| 6,767,362 | B2 | 7/2004 | Schreck | 623/2.11 |
| 6,769,434 | B2 | 8/2004 | Liddicoat et al. | 128/898 |
| 6,770,083 | B2 | 8/2004 | Seguin | 606/142 |
| 6,780,200 | B2 | 8/2004 | Jansen | 623/2.17 |
| 6,786,924 | B2 | 9/2004 | Ryan et al. | 623/2.36 |
| 6,786,925 | B1 | 9/2004 | Schoon et al. | 623/2.38 |
| 6,790,229 | B1 | 9/2004 | Berreklouw | 623/2.1 |
| 6,790,230 | B2 | 9/2004 | Beyersdorf et al. | 623/2.18 |
| 6,790,231 | B2 | 9/2004 | Liddicoat et al. | 623/2.37 |
| 6,793,673 | B2 | 9/2004 | Kowalsky et al. | 623/2.36 |
| 6,797,000 | B2 | 9/2004 | Simpson et al. | 623/2.15 |
| 6,797,001 | B2 | 9/2004 | Mathis et al. | 623/2.37 |
| 6,797,002 | B2 | 9/2004 | Spence et al. | 623/2.38 |
| 6,802,860 | B2 | 10/2004 | Cosgrove et al. | 623/2.11 |
| 6,805,710 | B2 | 10/2004 | Bolling et al. | 623/2.36 |
| 6,805,711 | B2 | 10/2004 | Quijano et al. | 623/2.37 |
| 6,810,882 | B2 | 11/2004 | Langberg et al. | 128/898 |
| 6,821,297 | B2 | 11/2004 | Snyders | 623/2.18 |
| 6,824,562 | B2 | 11/2004 | Mathis et al. | 623/2.36 |
| 6,830,584 | B1 | 12/2004 | Seguin | 623/2.11 |
| 6,830,585 | B1 | 12/2004 | Artof et al. | 623/2.11 |
| 6,837,902 | B2 | 1/2005 | Nguyen et al. | 623/2.13 |
| 6,840,246 | B2 | 1/2005 | Downing | 128/898 |
| 6,840,957 | B2 | 1/2005 | DiMatteo et al. | 623/1.24 |
| 6,846,324 | B2 | 1/2005 | Stobie | 623/2.11 |
| 6,846,325 | B2 | 1/2005 | Liddicoat | 623/2.4 |
| 6,858,039 | B2 | 2/2005 | McCarthy | 623/2.36 |
| 6,869,444 | B2 | 3/2005 | Gabbay | 623/2.36 |
| 6,872,226 | B2 | 3/2005 | Cali et al. | 623/2.13 |
| 6,875,224 | B2 | 4/2005 | Grimes | 606/219 |
| 6,875,230 | B1 | 4/2005 | Morita et al. | 623/2.12 |
| 6,875,231 | B2 | 4/2005 | Anduiza et al. | 623/2.14 |
| 6,881,199 | B2 | 4/2005 | Wilk et al. | 604/9 |
| 6,881,224 | B2 | 4/2005 | Kruse et al. | 623/2.11 |
| 6,883,522 | B2 | 4/2005 | Spence et al. | 128/898 |
| 6,890,352 | B1 | 5/2005 | Lentell | 623/2.27 |
| 6,890,353 | B2 | 5/2005 | Cohn et al. | 623/2.37 |
| 6,893,459 | B1 | 5/2005 | Macoviak | 623/2.11 |
| 6,893,460 | B2 | 5/2005 | Spenser et al. | 623/2.14 |
| 6,896,700 | B2 | 5/2005 | Lu et al. | 623/2.34 |
| 6,902,576 | B2 | 6/2005 | Drasler et al. | 623/1.24 |
| 6,908,478 | B2 | 6/2005 | Alferness et al. | 623/1.11 |
| 6,908,481 | B2 | 6/2005 | Cribier | 623/2.11 |
| 6,911,043 | B2 | 6/2005 | Myers et al. | 623/2.13 |
| 6,913,608 | B2 | 7/2005 | Liddicoat et al. | 606/151 |
| 6,916,338 | B2 | 7/2005 | Speziali | 623/2.12 |
| 6,918,917 | B1 | 7/2005 | Nguyen et al. | 606/139 |
| 6,921,407 | B2 | 7/2005 | Nguyen et al. | 606/142 |
| 6,921,811 | B2 | 7/2005 | Zamora et al. | 536/21 |
| 6,926,715 | B1 | 8/2005 | Hauck et al. | 606/41 |
| 6,926,730 | B1 | 8/2005 | Nguyen et al. | 606/213 |
| 6,929,653 | B2 | 8/2005 | Strecter | 606/200 |
| 6,932,838 | B2 | 8/2005 | Schwartz et al. | 623/1.23 |
| 6,936,067 | B2 | 8/2005 | Buchanan | 623/2.28 |
| 6,939,359 | B2 | 9/2005 | Tu et al. | 606/159 |
| 6,942,694 | B2 | 9/2005 | Liddicoat et al. | 623/2.36 |
| 6,945,957 | B2 | 9/2005 | Freyman | 604/96.01 |
| 6,945,978 | B1 | 9/2005 | Hyde | 606/142 |
| 6,945,996 | B2 | 9/2005 | Sedransk | 623/2.12 |
| 6,945,997 | B2 | 9/2005 | Huynh et al. | 623/2.17 |
| 6,949,122 | B2 | 9/2005 | Adams et al. | 623/2.36 |
| 6,951,571 | B1 | 10/2005 | Srivastava | 623/1.24 |
| 6,951,573 | B1 | 10/2005 | Dilling | 623/2.2 |
| 6,955,689 | B2 | 10/2005 | Ryan et al. | 623/2.36 |
| 6,958,076 | B2 | 10/2005 | Acosta et al. | 623/1.24 |
| 6,962,605 | B2 | 11/2005 | Cosgrove et al. | 623/2.36 |
| 6,964,682 | B2 | 11/2005 | Nguyen-Thien-Nhon et al. | 623/2.11 |
| 6,964,683 | B2 | 11/2005 | Kowalsky et al. | 623/2.36 |
| 6,964,684 | B2 | 11/2005 | Ortiz et al. | 623/2.37 |
| 6,966,925 | B2 | 11/2005 | Stobie | 623/2.11 |
| 6,966,926 | B2 | 11/2005 | Mathis | 623/2.36 |
| 6,974,464 | B2 | 12/2005 | Quijano et al. | 606/108 |
| 6,974,474 | B2 | 12/2005 | Pavcnik et al. | 623/1.24 |
| 6,974,476 | B2 | 12/2005 | McGuckin, Jr. et al. | 623/2.36 |
| 6,976,995 | B2 | 12/2005 | Mathis et al. | 623/2.37 |
| 6,979,350 | B2 | 12/2005 | Moll et al. | 623/1.24 |
| 6,986,775 | B2 | 1/2006 | Morales et al. | 606/139 |
| 6,989,027 | B2 | 1/2006 | Allen et al. | 623/2.18 |
| 6,989,028 | B2 | 1/2006 | Lashinski et al. | 623/2.37 |
| 6,997,950 | B2 | 2/2006 | Chawla | 623/2.1 |
| 6,997,951 | B2 | 2/2006 | Solem et al. | 623/2.37 |
| 7,004,176 | B2 | 2/2006 | Lau | 128/898 |
| 7,007,396 | B2 | 3/2006 | Rudko et al. | 33/512 |
| 7,011,669 | B2 | 3/2006 | Kimblad | 606/151 |
| 7,011,681 | B2 | 3/2006 | Vesely | 623/2.11 |
| 7,011,682 | B2 | 3/2006 | Lahsinski et al. | 623/2.37 |
| 7,018,406 | B2 | 3/2006 | Seguin | 623/2.1 |
| 7,018,407 | B1 | 3/2006 | Wright et al. | 623/2.11 |
| 7,018,408 | B2 | 3/2006 | Bailey et al. | 623/2.11 |
| 7,022,134 | B1 | 4/2006 | Quijano et al. | 623/1.24 |
| 7,025,780 | B2 | 4/2006 | Gabbay | 623/2.13 |
| 7,033,390 | B2 | 4/2006 | Johnson et al. | 623/2.11 |
| 7,037,333 | B2 | 5/2006 | Myers et al. | 623/2.13 |

| Patent No. | Date | Inventor(s) | Class |
|---|---|---|---|
| 7,037,334 B1 | 5/2006 | Hlavka et al. | 623/2.36 |
| 7,041,128 B2 | 5/2006 | McGuckin, Jr. et al. | 623/1.36 |
| 7,041,132 B2 | 5/2006 | Quijano et al. | 623/2.11 |
| 7,044,966 B2 | 5/2006 | Svanidze et al. | 623/2.1 |
| 7,044,967 B1 | 5/2006 | Solem et al. | 623/2.36 |
| 7,048,754 B2 | 5/2006 | Martin et al. | 606/232 |
| 7,048,757 B2 | 5/2006 | Shaknovich | 623/1.24 |
| 7,052,487 B2 | 5/2006 | Cohn et al. | 604/509 |
| 7,052,507 B2 | 5/2006 | Wakuda et al. | 606/194 |
| 7,063,722 B2 | 6/2006 | Marquez | 623/2.36 |
| 7,066,954 B2 | 6/2006 | Ryan et al. | 623/2.36 |
| 7,070,616 B2 | 7/2006 | Majercak et al. | 623/1.24 |
| 7,077,862 B2 | 7/2006 | Vidlund et al. | 623/2.36 |
| 7,081,131 B2 | 7/2006 | Thornton | 623/1.24 |
| 7,087,064 B1 | 8/2006 | Hyde | 606/142 |
| 7,089,051 B2 | 8/2006 | Jäverud et al. | 600/547 |
| 7,090,695 B2 | 8/2006 | Solem et al. | 623/2.37 |
| 2002/0013571 A1 | 1/2002 | Goldfarb et al. | 606/1 |
| 2002/0026216 A1 | 2/2002 | Grimes | 606/213 |
| 2002/0082630 A1 | 6/2002 | Menz et al. | 606/167 |
| 2002/0123802 A1 | 9/2002 | Snyders | 623/2.18 |
| 2002/0151970 A1 | 10/2002 | Garrison et al. | 623/2.11 |
| 2002/0183835 A1 | 12/2002 | Taylor et al. | 623/2.11 |
| 2002/0183838 A1 | 12/2002 | Liddicoat et al. | 623/2.11 |
| 2002/0198594 A1 | 12/2002 | Schreck | 623/2.11 |
| 2003/0050694 A1 | 3/2003 | Yang et al. | 623/2.11 |
| 2003/0130729 A1 | 7/2003 | Paniagua et al. | 623/2.11 |
| 2003/0163194 A1 | 8/2003 | Quijano et al. | 623/2.11 |
| 2003/0167071 A1 | 9/2003 | Martin et al. | 606/232 |
| 2003/0171806 A1 | 9/2003 | Mathis et al. | 623/2.36 |
| 2003/0199975 A1 | 10/2003 | Gabbay | 623/2.36 |
| 2003/0229394 A1 | 12/2003 | Ogle et al. | 623/2.14 |
| 2003/0229395 A1 | 12/2003 | Cox | 623/2.36 |
| 2003/0233142 A1 | 12/2003 | Morales et al. | 623/2.37 |
| 2003/0236568 A1 | 12/2003 | Hojeibane et al. | 623/1.24 |
| 2003/0236569 A1 | 12/2003 | Mathis et al. | 623/1.26 |
| 2004/0002719 A1 | 1/2004 | Oz et al. | 606/142 |
| 2004/0003819 A1 | 1/2004 | St. Goar et al. | 128/898 |
| 2004/0010305 A1 | 1/2004 | Alferness et al. | 623/1.15 |
| 2004/0015230 A1 | 1/2004 | Moll et al. | 623/1.24 |
| 2004/0015232 A1 | 1/2004 | Shu et al. | 623/2.4 |
| 2004/0015233 A1 | 1/2004 | Jansen | 623/2.18 |
| 2004/0019374 A1 | 1/2004 | Hojeibane et al. | 623/1.13 |
| 2004/0019377 A1 | 1/2004 | Taylor et al. | 623/2.11 |
| 2004/0019378 A1 | 1/2004 | Hlavka et al. | 623/2.11 |
| 2004/0024447 A1 | 2/2004 | Haverich | 623/1.24 |
| 2004/0024451 A1 | 2/2004 | Johnson et al. | 623/2.11 |
| 2004/0024452 A1 | 2/2004 | Kruse et al. | 623/2.13 |
| 2004/0030321 A1 | 2/2004 | Fangrow, Jr. | 604/533 |
| 2004/0030381 A1 | 2/2004 | Shu | 623/2.11 |
| 2004/0030382 A1 | 2/2004 | St. Goar et al. | 623/2.36 |
| 2004/0030405 A1 | 2/2004 | Carpentier et al. | 623/23.72 |
| 2004/0034380 A1 | 2/2004 | Woolfson et al. | 606/142 |
| 2004/0034411 A1 | 2/2004 | Quijano et al. | 623/2.11 |
| 2004/0039436 A1 | 2/2004 | Spenser et al. | 623/1.13 |
| 2004/0039442 A1 | 2/2004 | St. Goar et al. | 623/2.36 |
| 2004/0039443 A1 | 2/2004 | Solem et al. | 623/2.37 |
| 2004/0044350 A1 | 3/2004 | Martin et al. | 606/139 |
| 2004/0044365 A1 | 3/2004 | Bachman | 606/213 |
| 2004/0044403 A1 | 3/2004 | Bischoff et al. | 623/1.41 |
| 2004/0049207 A1 | 3/2004 | Goldfarb et al. | 606/139 |
| 2004/0049211 A1 | 3/2004 | Tremulis et al. | 606/153 |
| 2004/0049266 A1 | 3/2004 | Anduiza et al. | 623/2.11 |
| 2004/0059351 A1 | 3/2004 | Eigler et al. | 606/148 |
| 2004/0059411 A1 | 3/2004 | Strecker | 623/1.23 |
| 2004/0059412 A1 | 3/2004 | Lytle, IV et al. | 623/2.11 |
| 2004/0060161 A1 | 4/2004 | Leal et al. | 29/558 |
| 2004/0073301 A1 | 4/2004 | Donlon et al. | 623/2.11 |
| 2004/0073302 A1 | 4/2004 | Rourke et al. | 623/2.36 |
| 2004/0078072 A1 | 4/2004 | Tu et al. | 623/1.23 |
| 2004/0078074 A1 | 4/2004 | Anderson et al. | 623/2.11 |
| 2004/0082910 A1 | 4/2004 | Constantz et al. | 604/101.04 |
| 2004/0082923 A1 | 4/2004 | Field | 604/267 |
| 2004/0082991 A1 | 4/2004 | Nguyen et al. | 623/2.14 |
| 2004/0087975 A1 | 5/2004 | Lucatero et al. | 606/139 |
| 2004/0088045 A1 | 5/2004 | Cox | 623/2.13 |
| 2004/0088046 A1 | 5/2004 | Speziali | 623/2.19 |
| 2004/0092858 A1 | 5/2004 | Wilson et al. | 604/9 |
| 2004/0093060 A1 | 5/2004 | Seguin et al. | 623/1.11 |
| 2004/0093070 A1 | 5/2004 | Hojeibane et al. | 623/1.15 |
| 2004/0093080 A1 | 5/2004 | Helmus et al. | 623/2.41 |
| 2004/0097979 A1 | 5/2004 | Svanidze et al. | 606/151 |
| 2004/0098098 A1 | 5/2004 | McGuckin, Jr. et al. | 623/1.14 |
| 2004/0098112 A1 | 5/2004 | DiMatteo et al. | 623/1.24 |
| 2004/0102839 A1 | 5/2004 | Cohn et al. | 623/2.11 |
| 2004/0102840 A1 | 5/2004 | Solem et al. | 623/2.11 |
| 2004/0102842 A1 | 5/2004 | Jansen | 623/2.38 |
| 2004/0106976 A1 | 6/2004 | Bailey et al. | 623/1.11 |
| 2004/0106990 A1 | 6/2004 | Spence et al. | 623/2.11 |
| 2004/0106991 A1 | 6/2004 | Hopkins et al. | 623/2.13 |
| 2004/0111096 A1 | 6/2004 | Tu et al. | 606/108 |
| 2004/0117009 A1 | 6/2004 | Cali et al. | 623/2.12 |
| 2004/0122448 A1 | 6/2004 | Levine | 606/139 |
| 2004/0122512 A1 | 6/2004 | Navia et al. | 623/2.12 |
| 2004/0122513 A1 | 6/2004 | Navia et al. | 623/2.12 |
| 2004/0122514 A1 | 6/2004 | Fogarty et al. | 623/2.14 |
| 2004/0122515 A1 | 6/2004 | Chu | 623/2.29 |
| 2004/0122516 A1 | 6/2004 | Fogarty et al. | 623/2.37 |
| 2004/0127979 A1 | 7/2004 | Wilson et al. | 623/2.1 |
| 2004/0127980 A1 | 7/2004 | Kowalsky et al. | 623/2.11 |
| 2004/0127981 A1 | 7/2004 | Rahdert et al. | 623/2.36 |
| 2004/0127982 A1 | 7/2004 | Machold et al. | 623/2.36 |
| 2004/0133220 A1 | 7/2004 | Lashinski et al. | 606/151 |
| 2004/0133267 A1 | 7/2004 | Lane | 623/1.24 |
| 2004/0133273 A1 | 7/2004 | Cox | 623/2.11 |
| 2004/0138742 A1 | 7/2004 | Myers et al. | 623/2.12 |
| 2004/0138743 A1 | 7/2004 | Myers et al. | 623/2.13 |
| 2004/0138744 A1 | 7/2004 | Lashinski et al. | 623/2.36 |
| 2004/0138745 A1 | 7/2004 | Macoviak et al. | 623/2.36 |
| 2004/0148018 A1 | 7/2004 | Carpentier et al. | 623/2.18 |
| 2004/0148019 A1 | 7/2004 | Vidlund et al. | 623/2.36 |
| 2004/0148020 A1 | 7/2004 | Vidlund et al. | 623/2.36 |
| 2004/0153052 A1 | 8/2004 | Mathis | 606/1 |
| 2004/0153146 A1 | 8/2004 | Lashinski et al. | 623/2.36 |
| 2004/0153147 A1 | 8/2004 | Mathis | 623/2.37 |
| 2004/0158321 A1 | 8/2004 | Reuter et al. | 623/2.36 |
| 2004/0162610 A1 | 8/2004 | Liska et al. | 623/2.11 |
| 2004/0167539 A1 | 8/2004 | Kuehn et al. | 606/108 |
| 2004/0167620 A1 | 8/2004 | Ortiz et al. | 623/2.11 |
| 2004/0172046 A1 | 9/2004 | Hlavka et al. | 606/142 |
| 2004/0176839 A1 | 9/2004 | Huynh et al. | 623/2.4 |
| 2004/0176840 A1 | 9/2004 | Langberg et al. | 623/2.37 |
| 2004/0181238 A1 | 9/2004 | Zarbatany et al. | 606/142 |
| 2004/0186444 A1 | 9/2004 | Daly et al. | 604/247 |
| 2004/0186558 A1 | 9/2004 | Pavcnik et al. | 623/1.24 |
| 2004/0186561 A1 | 9/2004 | McGuckin, Jr. et al. | 623/1.36 |
| 2004/0186563 A1 | 9/2004 | Lobbi | 623/2.11 |
| 2004/0186565 A1 | 9/2004 | Schreck | 623/2.18 |
| 2004/0186566 A1 | 9/2004 | Hindrichs et al. | 623/2.37 |
| 2004/0193191 A1 | 9/2004 | Starksen et al. | 606/153 |
| 2004/0193253 A1 | 9/2004 | Thorpe et al. | 623/1.24 |
| 2004/0193260 A1 | 9/2004 | Alferness et al. | 623/2.11 |
| 2004/0199155 A1 | 10/2004 | Mollenauer | 606/27 |
| 2004/0199183 A1 | 10/2004 | Oz et al. | 606/142 |
| 2004/0199191 A1 | 10/2004 | Schwartz | 606/159 |
| 2004/0204758 A1 | 10/2004 | Eberhardt et al. | 623/2.15 |
| 2004/0206363 A1 | 10/2004 | McCarthy et al. | 128/898 |
| 2004/0210240 A1 | 10/2004 | Saint | 606/139 |
| 2004/0210301 A1 | 10/2004 | Obermiller | 623/1.24 |
| 2004/0210303 A1 | 10/2004 | Sedransk | 623/2.1 |
| 2004/0210304 A1 | 10/2004 | Seguin et al. | 623/2.11 |
| 2004/0210305 A1 | 10/2004 | Shu et al. | 623/2.11 |
| 2004/0210306 A1 | 10/2004 | Quijano et al. | 623/2.17 |
| 2004/0210307 A1 | 10/2004 | Khairkhahan | 623/2.18 |
| 2004/0215333 A1 | 10/2004 | Duran et al. | 623/1.24 |
| 2004/0215339 A1 | 10/2004 | Drasler et al. | 623/3.1 |
| 2004/0220654 A1 | 11/2004 | Mathis et al. | 623/1.11 |
| 2004/0220657 A1 | 11/2004 | Nieminen et al. | 623/1.15 |
| 2004/0225322 A1 | 11/2004 | Garrison et al. | 606/200 |
| 2004/0225344 A1 | 11/2004 | Hoffa et al. | 623/1.1 |
| 2004/0225348 A1 | 11/2004 | Case et al. | 623/1.15 |
| 2004/0225352 A1 | 11/2004 | Osborne et al. | 623/1.24 |
| 2004/0225353 A1 | 11/2004 | McGuckin, Jr. et al. | 623/2.11 |
| 2004/0225354 A1 | 11/2004 | Allen et al. | 623/2.11 |
| 2004/0225355 A1 | 11/2004 | Stevens | 623/2.11 |
| 2004/0225356 A1 | 11/2004 | Frater | 623/2.14 |
| 2004/0230117 A1 | 11/2004 | Tosaya et al. | 600/439 |
| 2004/0230297 A1 | 11/2004 | Thornton | 623/1.24 |

| Publication No. | Date | Inventor | Class |
|---|---|---|---|
| 2004/0236411 A1 | 11/2004 | Sarac et al. | 623/1.26 |
| 2004/0236418 A1 | 11/2004 | Stevens | 623/2.11 |
| 2004/0236419 A1 | 11/2004 | Milo | 623/2.36 |
| 2004/0243153 A1 | 12/2004 | Liddicoat et al. | 606/151 |
| 2004/0243219 A1 | 12/2004 | Fischer et al. | 623/1.15 |
| 2004/0243227 A1 | 12/2004 | Starksen et al. | 623/2.11 |
| 2004/0243228 A1 | 12/2004 | Kowalsky et al. | 623/2.11 |
| 2004/0243230 A1 | 12/2004 | Navia et al. | 623/2.36 |
| 2004/0254600 A1 | 12/2004 | Zarbatany et al. | 606/194 |
| 2004/0254636 A1 | 12/2004 | Flagle et al. | 623/1.24 |
| 2004/0260276 A1 | 12/2004 | Rudko et al. | 606/15 |
| 2004/0260317 A1 | 12/2004 | Bloom et al. | 606/151 |
| 2004/0260322 A1 | 12/2004 | Rudko et al. | 606/167 |
| 2004/0260389 A1 | 12/2004 | Case et al. | 623/1.24 |
| 2004/0260390 A1 | 12/2004 | Sarac et al. | 623/1.24 |
| 2004/0260393 A1 | 12/2004 | Rahdert et al. | 623/2.36 |
| 2004/0260394 A1 | 12/2004 | Douk et al. | 623/2.36 |
| 2004/0267357 A1 | 12/2004 | Allen et al. | 623/2.11 |
| 2005/0004583 A1 | 1/2005 | Oz et al. | 606/142 |
| 2005/0004667 A1 | 1/2005 | Swinford et al. | 623/2.36 |
| 2005/0010285 A1 | 1/2005 | Lambrecht et al. | 623/2.18 |
| 2005/0010287 A1 | 1/2005 | Macoviak et al. | 623/2.36 |
| 2005/0015112 A1 | 1/2005 | Cohn et al. | 606/200 |
| 2005/0021056 A1 | 1/2005 | St. Goar et al. | 606/144 |
| 2005/0021136 A1 | 1/2005 | Xie et al. | 623/2.14 |
| 2005/0027261 A1 | 2/2005 | Weaver et al. | 604/246 |
| 2005/0027348 A1 | 2/2005 | Case et al. | 623/1.24 |
| 2005/0027351 A1 | 2/2005 | Reuter et al. | 623/2.11 |
| 2005/0027353 A1 | 2/2005 | Alferness et al. | 623/2.11 |
| 2005/0033398 A1 | 2/2005 | Seguin | 623/1.11 |
| 2005/0033419 A1 | 2/2005 | Alferness et al. | 623/2.11 |
| 2005/0033446 A1 | 2/2005 | Deem et al. | 623/23.6 |
| 2005/0038506 A1 | 2/2005 | Webler et al. | 623/2.11 |
| 2005/0038507 A1 | 2/2005 | Alferness et al. | 623/2.11 |
| 2005/0043790 A1 | 2/2005 | Seguin | 623/2.18 |
| 2005/0043792 A1 | 2/2005 | Solem et al. | 623/2.36 |
| 2005/0049679 A1 | 3/2005 | Taylor et al. | 623/1.15 |
| 2005/0049692 A1 | 3/2005 | Numamoto et al. | 623/1.24 |
| 2005/0049696 A1 | 3/2005 | Siess et al. | 623/2.11 |
| 2005/0049697 A1 | 3/2005 | Sievers | 623/2.26 |
| 2005/0054977 A1 | 3/2005 | Laird et al. | 604/96.01 |
| 2005/0055079 A1 | 3/2005 | Duran | 623/1.13 |
| 2005/0055087 A1 | 3/2005 | Starksen | 623/2.11 |
| 2005/0055088 A1 | 3/2005 | Liddicoat et al. | 623/2.11 |
| 2005/0055089 A1 | 3/2005 | Macoviak et al. | 623/2.37 |
| 2005/0060029 A1 | 3/2005 | Le et al. | 623/2.11 |
| 2005/0060030 A1 | 3/2005 | Lashinski et al. | 623/2.37 |
| 2005/0065460 A1 | 3/2005 | Laird | 604/20 |
| 2005/0065550 A1 | 3/2005 | Starksen et al. | 606/219 |
| 2005/0065594 A1 | 3/2005 | Dimatteo et al. | 623/1.24 |
| 2005/0065597 A1 | 3/2005 | Lansac | 623/2.11 |
| 2005/0070998 A1 | 3/2005 | Rourke et al. | 623/2.11 |
| 2005/0075584 A1 | 4/2005 | Cali | 600/587 |
| 2005/0075659 A1 | 4/2005 | Realyvasquez et al. | 606/167 |
| 2005/0075662 A1 | 4/2005 | Pedersen et al. | 606/194 |
| 2005/0075712 A1 | 4/2005 | Biancucci et al. | 623/1.11 |
| 2005/0075713 A1 | 4/2005 | Biancucci et al. | 623/1.11 |
| 2005/0075717 A1 | 4/2005 | Nguyen et al. | 623/1.26 |
| 2005/0075718 A1 | 4/2005 | Nguyen et al. | 623/1.26 |
| 2005/0075719 A1 | 4/2005 | Bergheim | 623/1.26 |
| 2005/0075720 A1 | 4/2005 | Nguyen et al. | 623/1.26 |
| 2005/0075723 A1 | 4/2005 | Schroeder et al. | 623/2.1 |
| 2005/0075724 A1 | 4/2005 | Svanidze et al. | 623/2.11 |
| 2005/0075725 A1 | 4/2005 | Rowe | 623/2.14 |
| 2005/0075726 A1 | 4/2005 | Svanidze et al. | 623/2.14 |
| 2005/0075729 A1 | 4/2005 | Nguyen et al. | 623/2.18 |
| 2005/0075730 A1 | 4/2005 | Myers et al. | 623/2.18 |
| 2005/0075731 A1 | 4/2005 | Artof et al. | 623/2.18 |
| 2005/0080483 A1 | 4/2005 | Solem et al. | 623/2.11 |
| 2005/0085900 A1 | 4/2005 | Case et al. | 623/1.24 |
| 2005/0085903 A1 | 4/2005 | Lau | 623/2.11 |
| 2005/0085904 A1 | 4/2005 | Lemmon | 623/2.11 |
| 2005/0090846 A1 | 4/2005 | Pedersen et al. | 606/159 |
| 2005/0096735 A1 | 5/2005 | Hojeibane et al. | 623/1.24 |
| 2005/0096738 A1 | 5/2005 | Cali et al. | 623/2.18 |
| 2005/0096739 A1 | 5/2005 | Cao | 623/2.19 |
| 2005/0096740 A1 | 5/2005 | Langberg et al. | 623/2.36 |
| 2005/0101975 A1 | 5/2005 | Nguyen et al. | 606/151 |
| 2005/0102026 A1 | 5/2005 | Turner et al. | 623/2.1 |
| 2005/0107810 A1 | 5/2005 | Morales et al. | 606/143 |
| 2005/0107811 A1 | 5/2005 | Starksen et al. | 606/143 |
| 2005/0107812 A1 | 5/2005 | Starksen et al. | 606/143 |
| 2005/0107872 A1 | 5/2005 | Mensah et al. | 623/2.14 |
| 2005/0113910 A1 | 5/2005 | Paniagua et al. | 623/2.14 |
| 2005/0119673 A1 | 6/2005 | Gordon et al. | 606/151 |
| 2005/0119734 A1 | 6/2005 | Spence et al. | 623/2.11 |
| 2005/0119735 A1 | 6/2005 | Spence et al. | 623/2.36 |
| 2005/0125011 A1 | 6/2005 | Spence et al. | 606/144 |
| 2005/0131438 A1 | 6/2005 | Cohn | 606/170 |
| 2005/0137449 A1 | 6/2005 | Nieminen et al. | 600/37 |
| 2005/0137450 A1 | 6/2005 | Aronson et al. | 600/37 |
| 2005/0137451 A1 | 6/2005 | Gordon et al. | 600/37 |
| 2005/0137676 A1 | 6/2005 | Richardson et al. | 623/1.11 |
| 2005/0137681 A1 | 6/2005 | Shoemaker et al. | 623/1.23 |
| 2005/0137682 A1 | 6/2005 | Justino | 623/1.24 |
| 2005/0137685 A1 | 6/2005 | Nieminen et al. | 623/2.11 |
| 2005/0137686 A1 | 6/2005 | Salahieh et al. | 623/2.11 |
| 2005/0137688 A1 | 6/2005 | Salahieh et al. | 623/2.11 |
| 2005/0137689 A1 | 6/2005 | Salahieh et al. | 623/2.13 |
| 2005/0137690 A1 | 6/2005 | Salahieh et al. | 623/2.11 |
| 2005/0137691 A1 | 6/2005 | Salahieh et al. | 623/2.11 |
| 2005/0137692 A1 | 6/2005 | Haug et al. | 623/2.11 |
| 2005/0137693 A1 | 6/2005 | Haug et al. | 623/2.11 |
| 2005/0137694 A1 | 6/2005 | Haug et al. | 623/2.11 |
| 2005/0137696 A1 | 6/2005 | Salahieh et al. | 623/2.11 |
| 2005/0137697 A1 | 6/2005 | Salahieh et al. | 623/2.11 |
| 2005/0137698 A1 | 6/2005 | Salahieh et al. | 623/2.11 |
| 2005/0137699 A1 | 6/2005 | Salahieh et al. | 623/2.11 |
| 2005/0137700 A1 | 6/2005 | Spence et al. | 623/2.36 |
| 2005/0137701 A1 | 6/2005 | Salahieh et al. | 623/2.38 |
| 2005/0137702 A1 | 6/2005 | Haug et al. | 623/2.38 |
| 2005/0143807 A1 | 6/2005 | Pavcnik et al. | 623/1.24 |
| 2005/0143809 A1 | 6/2005 | Salahieh et al. | 623/2.11 |
| 2005/0143810 A1 | 6/2005 | Dauner et al. | 623/2.12 |
| 2005/0143811 A1 | 6/2005 | Realyvasquez | 623/2.36 |
| 2005/0149014 A1 | 7/2005 | Hauck et al. | 606/41 |
| 2005/0149179 A1 | 7/2005 | Mathis et al. | 623/2.11 |
| 2005/0149180 A1 | 7/2005 | Mathis et al. | 623/2.11 |
| 2005/0149181 A1 | 7/2005 | Eberhardt | 623/2.14 |
| 2005/0159810 A1 | 7/2005 | Filsoufi | 623/2.1 |
| 2005/0159811 A1 | 7/2005 | Lane | 623/2.14 |
| 2005/0165477 A1 | 7/2005 | Anduiza et al. | 623/2.11 |
| 2005/0165478 A1 | 7/2005 | Song | 623/2.22 |
| 2005/0171472 A1 | 8/2005 | Lutter | 604/101.03 |
| 2005/0171601 A1 | 8/2005 | Cosgrove et al. | 623/2.11 |
| 2005/0177227 A1 | 8/2005 | Heim et al. | 623/2.12 |
| 2005/0177228 A1 | 8/2005 | Solem et al. | 623/2.36 |
| 2005/0182483 A1 | 8/2005 | Osborne et al. | 623/1.24 |
| 2005/0184122 A1 | 8/2005 | Hlavka et al. | 227/175.1 |
| 2005/0187614 A1 | 8/2005 | Agnew | 623/1.24 |
| 2005/0187616 A1 | 8/2005 | Realyvasquez | 623/2.11 |
| 2005/0187617 A1 | 8/2005 | Navia | 623/2.13 |
| 2005/0192606 A1 | 9/2005 | Paul, Jr. et al. | 606/159 |
| 2005/0192665 A1 | 9/2005 | Spenser et al. | 623/2.11 |
| 2005/0197692 A1 | 9/2005 | Pai et al. | 623/2.1 |
| 2005/0197693 A1 | 9/2005 | Pai et al. | 623/2.1 |
| 2005/0197694 A1 | 9/2005 | Pai et al. | 623/2.1 |
| 2005/0203549 A1 | 9/2005 | Realyvasquez | 606/142 |
| 2005/0203605 A1 | 9/2005 | Dolan | 623/1.11 |
| 2005/0203614 A1 | 9/2005 | Forster et al. | 623/2.11 |
| 2005/0203615 A1 | 9/2005 | Forster et al. | 623/2.11 |
| 2005/0203616 A1 | 9/2005 | Cribier | 623/2.11 |
| 2005/0203617 A1 | 9/2005 | Forster et al. | 623/2.14 |
| 2005/0203618 A1 | 9/2005 | Sharkawy et al. | 623/2.38 |
| 2005/0216039 A1 | 9/2005 | Lederman | 606/144 |
| 2005/0216077 A1 | 9/2005 | Mathis et al. | 623/2.11 |
| 2005/0216078 A1 | 9/2005 | Starksen et al. | 623/2.11 |
| 2005/0222675 A1 | 10/2005 | Sauter | 623/1.26 |
| 2005/0222678 A1 | 10/2005 | Lashinski et al. | 623/2.11 |
| 2005/0228422 A1 | 10/2005 | Machold et al. | 606/167 |
| 2005/0228479 A1 | 10/2005 | Pavcnik et al. | 623/1.11 |
| 2005/0228486 A1 | 10/2005 | Case et al. | 623/1.24 |
| 2005/0228494 A1 | 10/2005 | Marquez | 623/2.18 |
| 2005/0228495 A1 | 10/2005 | Macoviak | 623/2.18 |
| 2005/0228496 A1 | 10/2005 | Mensah et al. | 623/2.41 |
| 2005/0234541 A1 | 10/2005 | Hunt et al. | 623/1.24 |
| 2005/0234546 A1 | 10/2005 | Nugent et al. | 623/2.11 |
| 2005/0240200 A1 | 10/2005 | Bergheim | 606/108 |

| Publication No. | Date | Inventor | Class |
|---|---|---|---|
| 2005/0240202 A1 | 10/2005 | Shennib et al. | 606/142 |
| 2005/0240255 A1 | 10/2005 | Schaeffer | 623/1.11 |
| 2005/0240259 A1 | 10/2005 | Sisken et al. | 623/1.36 |
| 2005/0240262 A1 | 10/2005 | White | 623/2.12 |
| 2005/0244460 A1 | 11/2005 | Alferiev et al. | 424/426 |
| 2005/0246013 A1 | 11/2005 | Gabbay | 623/2.1 |
| 2005/0251251 A1 | 11/2005 | Cribier | 623/2.11 |
| 2005/0256566 A1 | 11/2005 | Gabbay | 623/2.1 |
| 2005/0261704 A1 | 11/2005 | Mathis | 606/108 |
| 2005/0261759 A1 | 11/2005 | Lambrecht et al. | 623/1.26 |
| 2005/0267493 A1 | 12/2005 | Schreck et al. | 606/139 |
| 2005/0267560 A1 | 12/2005 | Bates | 623/1.1 |
| 2005/0267565 A1 | 12/2005 | Dave et al. | 623/1.15 |
| 2005/0267571 A1 | 12/2005 | Spence et al. | 623/2.11 |
| 2005/0267573 A9 | 12/2005 | Macoviak et al. | 623/2.36 |
| 2005/0267574 A1 | 12/2005 | Cohn et al. | 623/2.36 |
| 2005/0272969 A1 | 12/2005 | Alferness et al. | 600/37 |
| 2005/0273160 A1 | 12/2005 | Lashinski et al. | 623/1.25 |
| 2005/0278015 A1 | 12/2005 | Dave et al. | 623/1.38 |
| 2005/0283178 A1 | 12/2005 | Flagle et al. | 606/191 |
| 2005/0288779 A1 | 12/2005 | Shaoulian et al. | 623/2.37 |
| 2006/0000715 A1 | 1/2006 | Whitcher et al. | 205/80 |
| 2006/0004439 A1 | 1/2006 | Spenser et al. | 623/1.23 |
| 2006/0004442 A1 | 1/2006 | Spenser et al. | 623/2.11 |
| 2006/0009841 A1 | 1/2006 | McGuckin, Jr. et al. | 623/2.38 |
| 2006/0009842 A1 | 1/2006 | Huynh et al. | 623/2.41 |
| 2006/0013805 A1 | 1/2006 | Hebbel et al. | 424/93.21 |
| 2006/0013855 A1 | 1/2006 | Carpenter et al. | 424/423 |
| 2006/0015136 A1 | 1/2006 | Besselink | 606/200 |
| 2006/0015178 A1 | 1/2006 | Moaddeb et al. | 623/2.36 |
| 2006/0015179 A1 | 1/2006 | Bulman-Fleming et al. | 623/2.36 |
| 2006/0020275 A1 | 1/2006 | Goldfarb et al. | 606/151 |
| 2006/0020327 A1 | 1/2006 | Lashinski et al. | 623/1.25 |
| 2006/0020332 A1 | 1/2006 | Lashinski et al. | 623/2.11 |
| 2006/0020334 A1 | 1/2006 | Lashinski et al. | 623/2.11 |
| 2006/0020335 A1 | 1/2006 | Kowalsky et al. | 623/2.36 |
| 2006/0020336 A1 | 1/2006 | Liddicoat | 623/2.37 |
| 2006/0025750 A1 | 2/2006 | Startksen et al. | 604/510 |
| 2006/0025784 A1 | 2/2006 | Startksen et al. | 606/151 |
| 2006/0025787 A1 | 2/2006 | Morales et al. | 606/151 |
| 2006/0025854 A1 | 2/2006 | Lashinski et al. | 623/1.25 |
| 2006/0025855 A1 | 2/2006 | Lashinski et al. | 623/2.1 |
| 2006/0025856 A1 | 2/2006 | Ryan et al. | 623/2.11 |
| 2006/0025857 A1 | 2/2006 | Bergheim et al. | 623/2.18 |
| 2006/0030747 A1 | 2/2006 | Kantrowitz et al. | 600/16 |
| 2006/0030866 A1 | 2/2006 | Schreck | 606/139 |
| 2006/0030882 A1 | 2/2006 | Adams et al. | 606/219 |
| 2006/0030885 A1 | 2/2006 | Hyde | 606/232 |
| 2006/0036317 A1 | 2/2006 | Vidlund et al. | 623/2.36 |
| 2006/0041305 A1 | 2/2006 | Lauterjung | 623/1.36 |
| 2006/0041306 A1 | 2/2006 | Vidlund et al. | 623/2.11 |
| 2006/0047297 A1 | 3/2006 | Case | 606/142 |
| 2006/0047338 A1 | 3/2006 | Jenson | 623/2.11 |
| 2006/0047343 A1 | 3/2006 | Oviatt et al. | 623/915 |
| 2006/0052804 A1 | 3/2006 | Mialhe | 606/157 |
| 2006/0052867 A1 | 3/2006 | Revuelta et al. | 623/2.18 |
| 2006/0058817 A1 | 3/2006 | Starksen et al. | 606/142 |
| 2006/0058865 A1 | 3/2006 | Case et al. | 623/1.11 |
| 2006/0058871 A1 | 3/2006 | Zakay et al. | 623/2.18 |
| 2006/0058889 A1 | 3/2006 | Case et al. | 623/23.68 |
| 2006/0064115 A1 | 3/2006 | Allen et al. | 606/139 |
| 2006/0064116 A1 | 3/2006 | Allen et al. | 606/139 |
| 2006/0064118 A1 | 3/2006 | Kimblad | 606/151 |
| 2006/0064174 A1 | 3/2006 | Zadno | 623/23.68 |
| 2006/0069400 A1 | 3/2006 | Burnett et al. | 606/153 |
| 2006/0069430 A9 | 3/2006 | Rahdert et al. | 623/2.36 |
| 2006/0074483 A1 | 4/2006 | Schrayer | 623/2.1 |
| 2006/0074484 A1 | 4/2006 | Huber | 623/2.11 |
| 2006/0074485 A1 | 4/2006 | Realyvasquez | 623/2.11 |
| 2006/0085060 A1 | 4/2006 | Campbell | 623/1.26 |
| 2006/0089708 A1 | 4/2006 | Osse et al. | 623/1.24 |
| 2006/0095115 A1 | 5/2006 | Bladillah et al. | 623/1.16 |
| 2006/0095125 A1 | 5/2006 | Chinn et al. | 623/2.4 |
| 2006/0099326 A1 | 5/2006 | Keogh et al. | 427/2.36 |
| 2006/0100697 A1 | 5/2006 | Casanova | 623/2.11 |
| 2006/0100699 A1 | 5/2006 | Vidlund et al. | 623/2.36 |
| 2006/0106278 A1 | 5/2006 | Machold et al. | 600/37 |
| 2006/0106279 A1 | 5/2006 | Machold et al. | 600/37 |
| 2006/0106456 A9 | 5/2006 | Machold et al. | 623/2.36 |
| 2006/0111660 A1 | 5/2006 | Wolf et al. | 604/9 |
| 2006/0111773 A1 | 5/2006 | Rittgers et al. | 623/1.24 |
| 2006/0111774 A1 | 5/2006 | Samkov et al. | 623/2.25 |
| 2006/0116572 A1 | 6/2006 | Case | 600/424 |
| 2006/0116756 A1 | 6/2006 | Solem et al. | 623/2.11 |
| 2006/0122686 A1 | 6/2006 | Gilad et al. | 623/1.13 |
| 2006/0122692 A1 | 6/2006 | Gilad et al. | 623/1.24 |
| 2006/0122693 A1 | 6/2006 | Biadillah et al. | 623/1.24 |
| 2006/0127443 A1 | 6/2006 | Helmus | 424/423 |
| 2006/0129235 A1 | 6/2006 | Seguin et al. | 623/2.11 |
| 2006/0129236 A1 | 6/2006 | McCarthy | 623/2.36 |
| 2006/0135476 A1 | 6/2006 | Kutryk et al. | 514/59 |
| 2006/0135964 A1 | 6/2006 | Vesely | 606/108 |
| 2006/0135967 A1 | 6/2006 | Realyvasquez | 606/142 |
| 2006/0136044 A1 | 6/2006 | Osborne | 623/1.24 |
| 2006/0136045 A1 | 6/2006 | Flagle et al. | 623/1.24 |
| 2006/0136052 A1 | 6/2006 | Vesely | 623/2.18 |
| 2006/0136054 A1 | 6/2006 | Berg et al. | 623/2.38 |
| 2006/0142846 A1 | 6/2006 | Pavcnik et al. | 623/1.24 |
| 2006/0142847 A1 | 6/2006 | Shaknovich | 623/1.24 |
| 2006/0142848 A1 | 6/2006 | Gabbay | 623/1.26 |
| 2006/0142854 A1 | 6/2006 | Alferness et al. | 623/2.11 |
| 2006/0149358 A1 | 7/2006 | Zilla et al. | 623/1.22 |
| 2006/0149360 A1 | 7/2006 | Schwammenthal et al. | 623/1.24 |
| 2006/0149367 A1 | 7/2006 | Sieracki | 623/2.21 |
| 2006/0149368 A1 | 7/2006 | Spence | 623/2.37 |
| 2006/0161133 A1 | 7/2006 | Laird et al. | 604/509 |
| 2006/0161248 A1 | 7/2006 | Case et al. | 623/2.1 |
| 2006/0161250 A1 | 7/2006 | Shaw | 623/2.17 |
| 2006/0167468 A1 | 7/2006 | Gabbay | 606/108 |
| 2006/0167541 A1 | 7/2006 | Lattouf | 623/2.11 |
| 2006/0167542 A1 | 7/2006 | Quintessenza | 623/2.12 |
| 2006/0167543 A1 | 7/2006 | Bailey et al. | 623/2.18 |

FOREIGN PATENT DOCUMENTS

| | | |
|---|---|---|
| EP | 0 466 518 | 1/1992 |
| FR | 2 728 457 | 6/1996 |
| WO | WO 88/00459 | 1/1988 |
| WO | WO 90/15582 | 12/1990 |
| WO | WO 95/01669 | 1/1995 |
| WO | WO 96/19159 | 6/1996 |
| WO | WO 98/03656 | 1/1998 |
| WO | WO 98/46115 | 10/1998 |
| WO | WO 99/04724 | 2/1999 |
| WO | WO 00/67679 | 11/2000 |
| WO | WO 01/15650 | 3/2001 |
| WO | WO 01/17462 | 3/2001 |
| WO | WO 03/047468 | 6/2003 |
| WO | WO 03/084443 | 10/2003 |
| WO | WO 2004/019825 | 3/2004 |
| WO | WO 2004/021893 | 3/2004 |
| WO | WO 2004/023980 | 3/2004 |
| WO | WO 2004/030568 | 4/2004 |
| WO | WO 2004/030569 | 4/2004 |
| WO | WO 2004/030570 | 4/2004 |
| WO | WO 2004/032724 | 4/2004 |
| WO | WO 2004/032796 | 4/2004 |
| WO | WO 2004/037128 | 5/2004 |
| WO | WO 2004/037317 | 5/2004 |
| WO | WO 2004/039432 | 5/2004 |
| WO | WO 2004/043265 | 5/2004 |
| WO | WO 2004/043273 | 5/2004 |
| WO | WO 2004/043293 | 5/2004 |
| WO | WO 2004/045370 | 6/2004 |
| WO | WO 2004/045378 | 6/2004 |
| WO | WO 2004/045463 | 6/2004 |
| WO | WO 2004/060217 | 7/2004 |
| WO | WO 2004/060470 | 7/2004 |
| WO | WO 2004/062725 | 7/2004 |
| WO | WO 2004/066803 | 8/2004 |
| WO | WO 2004/066826 | 8/2004 |
| WO | WO 2004/069287 | 8/2004 |
| WO | WO 2004/075789 | 9/2004 |
| WO | WO 2004/080352 | 9/2004 |
| WO | WO 2004/082523 | 9/2004 |
| WO | WO 2004/082527 | 9/2004 |
| WO | WO 2004/082528 | 9/2004 |
| WO | WO 2004/082536 | 9/2004 |

| | | | | | | |
|---|---|---|---|---|---|---|
| WO | WO 2004/082537 | 9/2004 | | WO | WO 2005/055883 | 6/2005 |
| WO | WO 2004/082538 | 9/2004 | | WO | WO 2005/058206 | 6/2005 |
| WO | WO 2004/082757 | 9/2004 | | WO | WO 2005/065585 | 7/2005 |
| WO | WO 2004/084746 | 10/2004 | | WO | WO 2005/065593 | 7/2005 |
| WO | WO 2004/084770 | 10/2004 | | WO | WO 2005/065594 | 7/2005 |
| WO | WO 2004/089246 | 10/2004 | | WO | WO 2005/070342 | 8/2005 |
| WO | WO 2004/089250 | 10/2004 | | WO | WO 2005/070343 | 8/2005 |
| WO | WO 2004/089253 | 10/2004 | | WO | WO 2005/072654 | 8/2005 |
| WO | WO 2004/091449 | 10/2004 | | WO | WO 2005/072655 | 8/2005 |
| WO | WO 2004/091454 | 10/2004 | | WO | WO 2005/079706 | 9/2005 |
| WO | WO 2004/093638 | 11/2004 | | WO | WO 2005/082288 | 9/2005 |
| WO | WO 2004/093726 | 11/2004 | | WO | WO 2005/082289 | 9/2005 |
| WO | WO 2004/093728 | 11/2004 | | WO | WO 2005/084595 | 9/2005 |
| WO | WO 2004/093730 | 11/2004 | | WO | WO 2005/087139 | 9/2005 |
| WO | WO 2004/093745 | 11/2004 | | WO | WO 2005/087140 | 9/2005 |
| WO | WO 2004/093935 | 11/2004 | | WO | WO 2006/000763 | 1/2006 |
| WO | WO 2004/096100 | 11/2004 | | WO | WO 2006/000776 | 1/2006 |
| WO | WO 2004/103222 | 12/2004 | | WO | WO 2006/002492 | 1/2006 |
| WO | WO 2004/103223 | 12/2004 | | WO | WO 2006/004679 | 1/2006 |
| WO | WO 2004/105584 | 12/2004 | | WO | WO 2006/005015 | 1/2006 |
| WO | WO 2004/105651 | 12/2004 | | WO | WO 2006/009690 | 1/2006 |
| WO | WO 2004/112582 | 12/2004 | | WO | WO 2006/011127 | 2/2006 |
| WO | WO 2004/112585 | 12/2004 | | WO | WO 2006/012011 | 2/2006 |
| WO | WO 2004/112643 | 12/2004 | | WO | WO 2006/012013 | 2/2006 |
| WO | WO 2004/112652 | 12/2004 | | WO | WO 2006/012038 | 2/2006 |
| WO | WO 2004/112657 | 12/2004 | | WO | WO 2006/012068 | 2/2006 |
| WO | WO 2004/112658 | 12/2004 | | WO | WO 2006/012322 | 2/2006 |
| WO | WO 2004/002466 | 1/2005 | | WO | WO 2006/019498 | 2/2006 |
| WO | WO 2005/000152 | 1/2005 | | WO | WO 2006/026371 | 3/2006 |
| WO | WO 2005/002424 | 1/2005 | | WO | WO 2006/026377 | 3/2006 |
| WO | WO 2005/004753 | 1/2005 | | WO | WO 2006/026912 | 3/2006 |
| WO | WO 2005/007017 | 1/2005 | | WO | WO 2006/027499 | 3/2006 |
| WO | WO 2005/007018 | 1/2005 | | WO | WO 2006/028821 | 3/2006 |
| WO | WO 2005/007036 | 1/2005 | | WO | WO 2006/029062 | 3/2006 |
| WO | WO 2005/007037 | 1/2005 | | WO | WO 2006/031436 | 3/2006 |
| WO | WO 2005/009285 | 2/2005 | | WO | WO 2006/031469 | 3/2006 |
| WO | WO 2005/009286 | 2/2005 | | WO | WO 2006/032051 | 3/2006 |
| WO | WO 2005/009505 | 2/2005 | | WO | WO 2006/034245 | 3/2006 |
| WO | WO 2005/009506 | 2/2005 | | WO | WO 2006/035415 | 4/2006 |
| WO | WO 2005/011473 | 2/2005 | | WO | WO 2006/041505 | 4/2006 |
| WO | WO 2005/011534 | 2/2005 | | WO | WO 2006/044679 | 4/2006 |
| WO | WO 2005/011535 | 2/2005 | | WO | WO 2006/048664 | 5/2006 |
| WO | WO 2005/013860 | 2/2005 | | WO | WO 2006/050459 | 5/2006 |
| WO | WO 2005/018507 | 3/2005 | | WO | WO 2006/050460 | 5/2006 |
| WO | WO 2005/021063 | 3/2005 | | WO | WO 2006/054107 | 5/2006 |
| WO | WO 2005/023155 | 3/2005 | | WO | WO 2006/054930 | 5/2006 |
| WO | WO 2005/025644 | 3/2005 | | WO | WO 2006/055982 | 5/2006 |
| WO | WO 2005/027790 | 3/2005 | | WO | WO 2006/060546 | 6/2006 |
| WO | WO 2005/027797 | 3/2005 | | WO | WO 2006/063108 | 6/2006 |
| WO | WO 2005/034812 | 4/2005 | | WO | WO 2006/063181 | 6/2006 |
| WO | WO 2005/039428 | 5/2005 | | WO | WO 2006/063199 | 6/2006 |
| WO | WO 2005/039452 | 5/2005 | | WO | WO 2006/064490 | 6/2006 |
| WO | WO 2005/046488 | 5/2005 | | WO | WO 2006/065212 | 6/2006 |
| WO | WO 2005/046528 | 5/2005 | | WO | WO 2006/065930 | 6/2006 |
| WO | WO 2005/046529 | 5/2005 | | WO | WO 2006/066148 | 6/2006 |
| WO | WO 2005/046530 | 5/2005 | | WO | WO 2006/066150 | 6/2006 |
| WO | WO 2005/046531 | 5/2005 | | WO | WO 2006/069094 | 6/2006 |
| WO | WO 2005/048883 | 6/2005 | | WO | WO 2006/070372 | 7/2006 |
| WO | WO 2005/049103 | 6/2005 | | WO | WO 2006/073628 | 7/2006 |
| WO | WO 2005/051226 | 6/2005 | | WO | WO 2006/076890 | 7/2006 |
| WO | WO 2005/055811 | 6/2005 | | WO | WO 2004/047677 | 6/2007 |

CARDIAC VALVE, SYSTEM, AND METHOD

PRIORITY INFORMATION

This application is a continuation of U.S. application Ser. No. 10/933,088, filed Sep. 2, 2004, the specification of which is incorporated herein by reference.

FIELD OF THE INVENTION

The present invention relates generally to apparatus, systems, and methods for use in a lumen; and more particularly to cardiac valves, systems, and methods for use in the vasculature system.

BACKGROUND OF THE INVENTION

Diseases of the heart valves are grouped according to which valve(s) are involved and the way that blood flow is disrupted. The most common valve problems occur in the mitral and aortic valves. Diseases of the tricuspid and pulmonary valves are fairly rare.

The aortic valve regulates the blood flow from the heart's left ventricle into the aorta. The aorta is the main vessel that supplies oxygenated blood to the rest of the body. Diseases of the aorta can have a significant impact on an individual. Examples of such diseases include aortic regurgitation and aortic stenosis.

Aortic regurgitation is also called aortic insufficiency or aortic incompetence. It is a condition in which blood flows backward from a widened or weakened aortic valve into the left ventricle of the heart. In its most serious form, aortic regurgitation is caused by an infection that leaves holes in the valve leaflets. Symptoms of aortic regurgitation may not appear for years. When symptoms do appear, it is because the left ventricle must work harder as compared to an uncompromised ventricle to make up for the backflow of blood. The ventricle eventually gets larger and fluid backs up.

Aortic stenosis is a narrowing or blockage of the aortic valve. Aortic stenosis occurs when the valve leaflets of the aorta become coated with deposits. The deposits change the shape of the leaflets and reduce blood flow through the valve. The left ventricle has to work harder as compared to an uncompromised ventricle to make up for the reduced blood flow. Over time, the extra work can weaken the heart muscle.

DETAILED DESCRIPTION

Figure 1A:
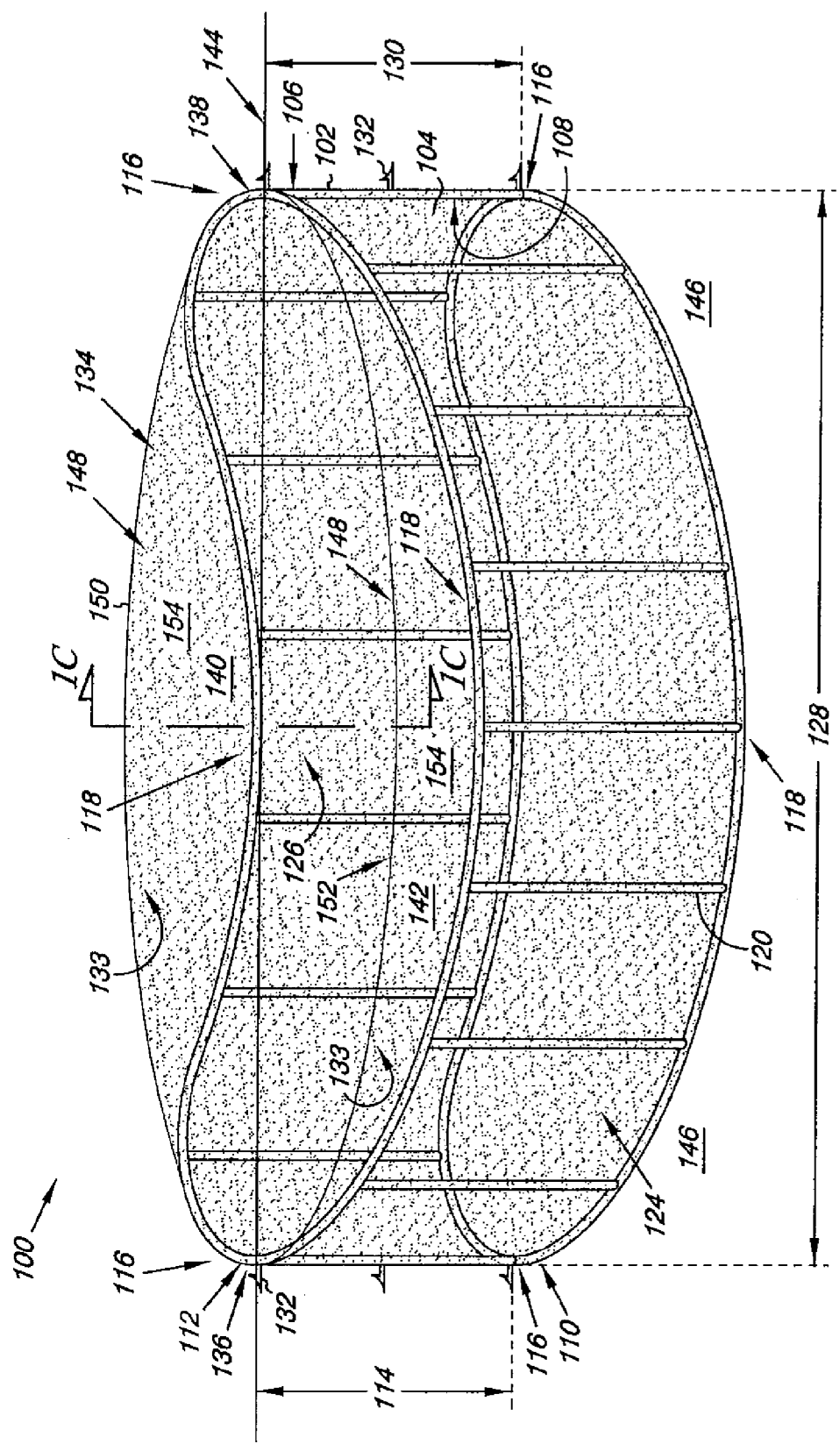
FIGS. 1A-1D illustrate an embodiment of a valve in perspective view.

Embodiments of the present invention are directed to an apparatus, system, and method for cardiac valve replacement and/or augmentation. For example, the apparatus can include a cardiac valve that can be used to replace an incompetent valve in a body lumen. Embodiments of the cardiac valve can include a support frame and cover that can be implanted through minimally-invasive techniques into a body lumen, such as an artery or a vein. In one example, embodiments of the present invention may help to augment or replace the function of a cardiac valve of individuals having heart valve disease.

The Figures herein follow a numbering convention in which the first digit or digits correspond to the drawing Figure number and the remaining digits identify an element or component in the drawing. Similar elements or components between different Figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide any number of additional embodiments of valve.

Various embodiments of the invention are illustrated in the figures. Generally, the cardiac valve can be implanted within the fluid passageway of a body lumen, such as for replacement of a cardiac valve structure within the body lumen (e.g., an aortic valve at the aortic root), to regulate the flow of a bodily fluid through the body lumen in a single direction.

Figure 1B:
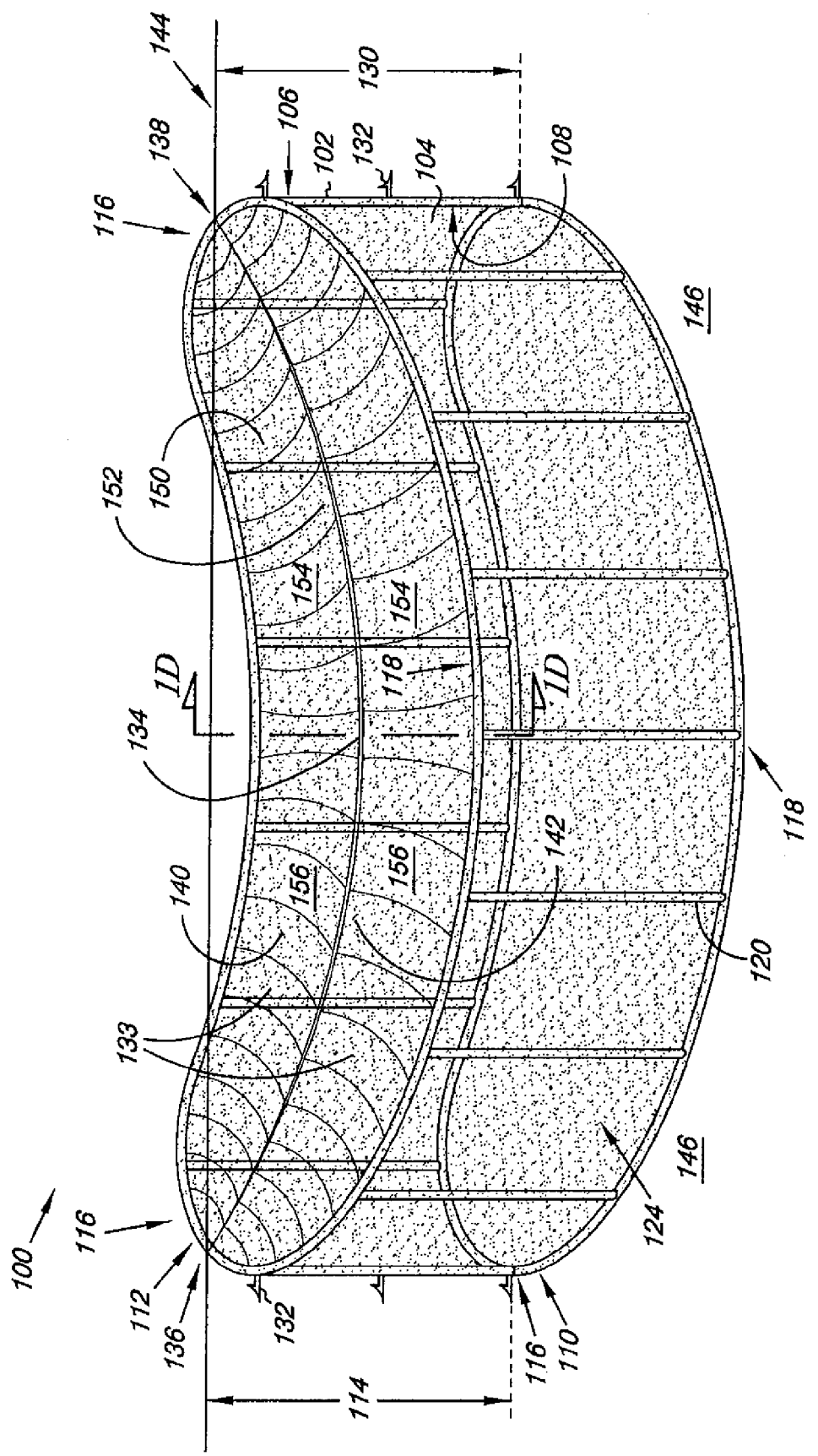
Figure 1C:
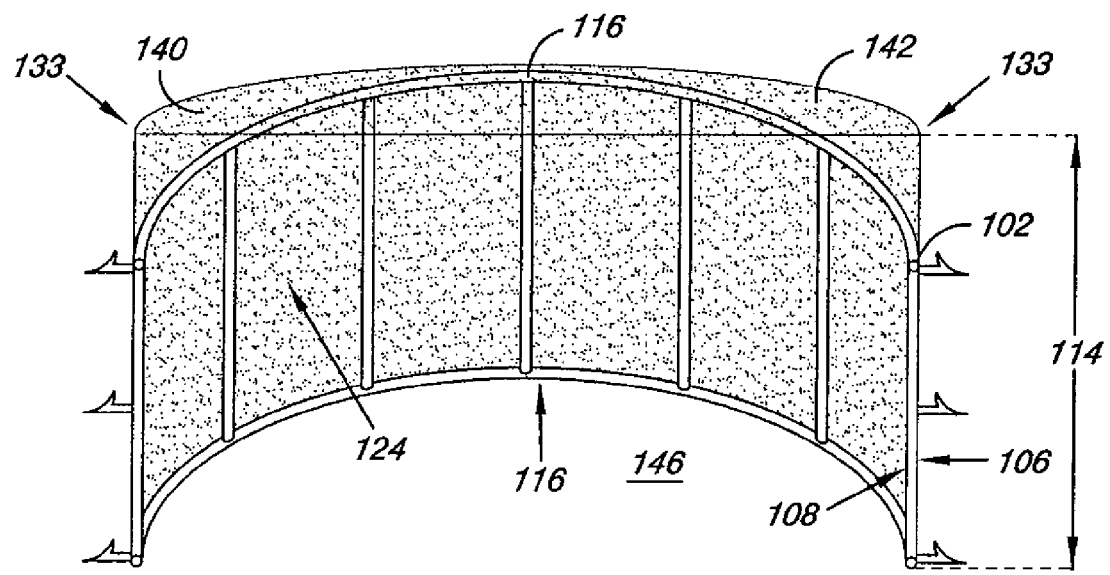
Figure 1D:
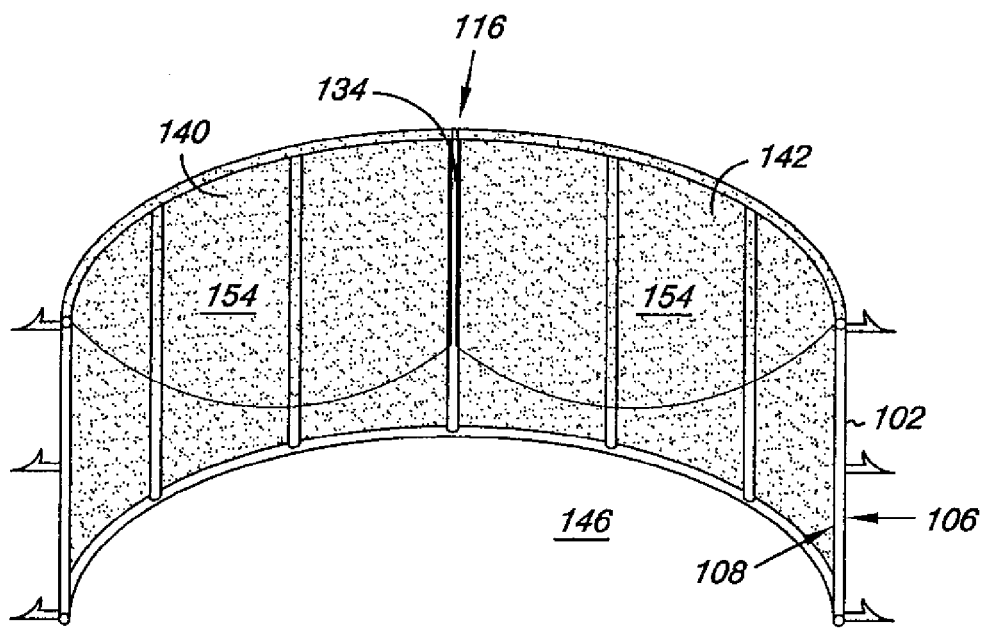

FIGS. 1A and 1B illustrate one embodiment of a cardiac valve 100. FIGS. 1A and 1B provide a perspective illustration of valve 100 in an open configuration (FIG. 1A) and a closed configuration (FIG. 1B). FIGS. 1C and 1D provide a sectional view of FIGS. 1A and 1B, respectively, to more clearly illustrate the embodiment of the cardiac valve 100.

Cardiac valve 100 includes a support frame 102 and a cover 104. The support frame 102 includes an outer surface 106 and an inner surface 108. The support frame 102 further includes a first end member 110 and a second end member 112 opposing the first end member 110. In one embodiment, the first end member 110 and the second end member 112 are in a substantially fixed distance relationship 114. As used herein, a substantially fixed distance relationship 114 indicates a fixed distance between the members 110 and 112 that may include variations of the fixed distance relationship inherently resulting from the manufacture of the articles of the present invention. In addition, the substantially fixed distance relationship 114 need not be consistent around the circumference of the cardiac valve 100. For example, the substantially fixed distance relationship 114 can be varied up to a predetermined percentage of an average valve diameter of the substantially fixed distance relationship 114. In one embodiment, the predetermined percentage can be up to seventy (70) percent (%).

The support frame 102 further includes an open frame configuration in which the first end member 110 and the second end member 112 define a sequence of convex curves 116 and concave curves 118. In one embodiment, the sequence of convex curves 116 and concave curves 118 are arranged such that the first end member 110 and the second end member 112 provide mirror images of each other set apart by the substantially fixed distance relationship 114. In another embodiment, the sequence of convex curves 116 and concave curves 118 are arranged such that the first end member 110 and the second end member 112 are substantially parallel. In an alternative embodiment, the sequence of convex curves 116 and concave curves 118 are arranged such that the relative position of the first end member 110 and the second end member 112 can have a variation from about zero (0) percent to about two hundred (200) percent variation as compared to an average distance or a preselected distance between the members 110 and 112. In one embodiment, the valve can be about twenty (20) to eighty (80) percent. As will be appreciated, the selection of these percentage values can be based on the anatomical location into which the valve is to be placed.

Figure 2A:
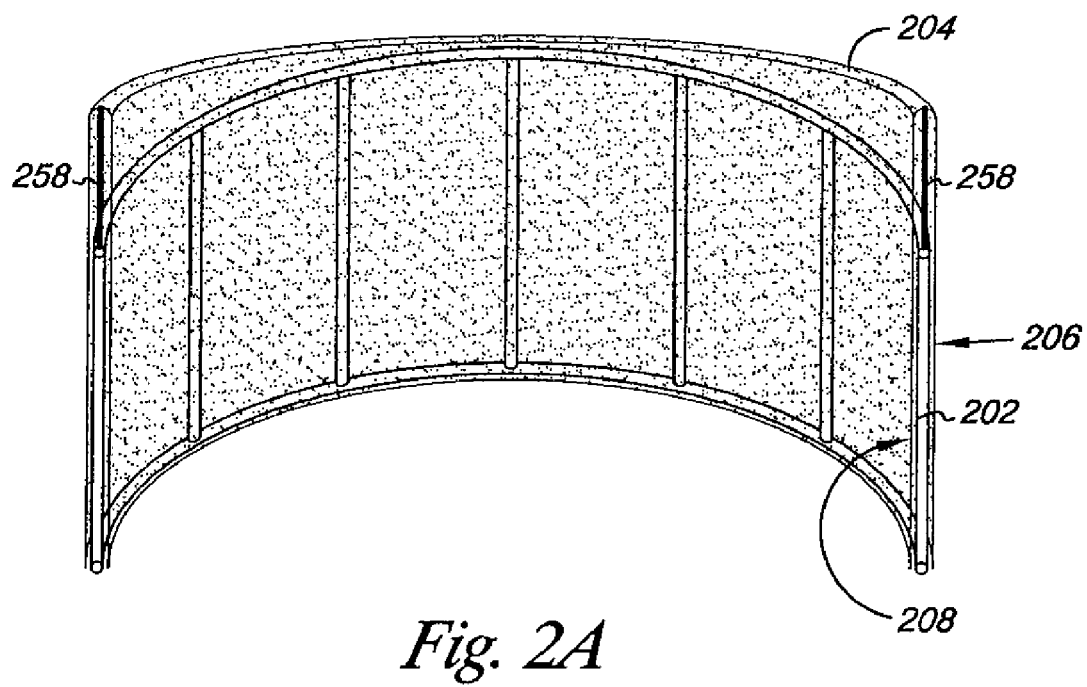
FIGS. 2A-2B illustrate another embodiment of a valve in perspective view.
Figure 2B:
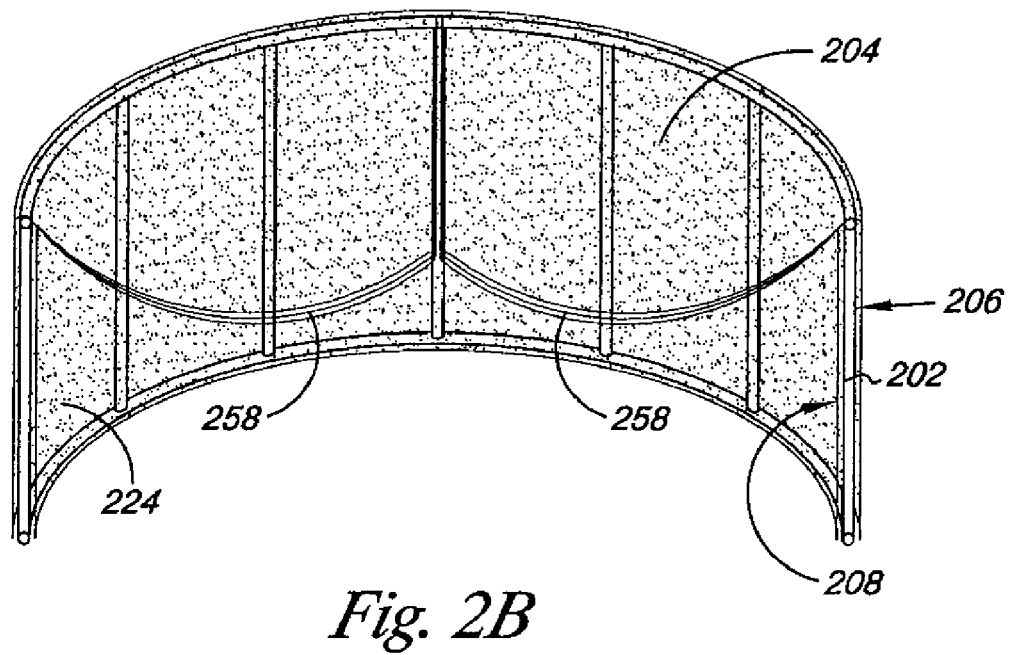

As illustrated in FIGS. 1A and 1B, the sequence of convex curves 116 and concave curves 118 of the first and second end members 110 and 112 can transition between each other with a uniform radius of curvature for each of the convex curves 116 and concave curves 118. Alternatively, the sequence of convex curves 116 and concave curves 118 transition between each other in a non-uniform manner. For example, the convex curves 116 can have a radius of curvature that is different (e.g., smaller) than the radius of curvature for the concave curves 118 (FIGS. 2A and 2B). Further, the shape and relationship of the convex curves 116 and concave curves 118 for each of the first end member 110 and the second end member 112 need not be symmetrical relative to each other, rather they may provide for a non-symmetrical relationship, which may vary around the circumference.

The support frame 102 can further include cross-members 120 coupled to the first end member 110 and the second end member 112. In one embodiment, cross-members 120 help to maintain the first end member 110 and the second end member 112 in the substantially fixed distance relationship 114. In one embodiment, the cross-members 120 can include a cross-sectional shape and can be formed from the same or similar materials as the end members 110 and 112, as discussed herein. In addition, the cross-members 120 can include any number of configurations, including linear configurations in which cross member 120 are arranged in parallel relative to other cross-members 120. Other configurations include, but are not limited to, curved configurations, configurations including one or more bends in the cross member 120, and configurations that include coil configurations. Other configurations are also possible. In addition, the cross-members 120 can further include additional members spanning between the cross-members 120 and/or the end members 110 and 112, as will be discussed herein.

The support frame 102 can be formed from a wide variety of materials and in a wide variety of configurations. Generally, support frame 102 can have a unitary structure with an open frame configuration. For example, the open frame configuration can include frame members (e.g., first end member 110 and a second end member 112, cross-members 120) that define openings 124 through the support frame 102. The support frame 102 can also be self-expanding. Examples of self-expanding frames include those formed from temperature-sensitive memory alloy which changes shape at a designated temperature or temperature range. Alternatively, the self-expanding frames can include those having a spring-bias. In addition, the support frame 102 can have a configuration that allows the frame 102 to be radially expandable through the use of a balloon catheter.

While the support frame 102 illustrated herein is shown having a circular configuration, other configurations are also possible. For example, the support frame 102 can also include an elliptical configuration, or other configurations that can accommodate the physiological structure in which the support frame 102 is to be placed. In addition, the support frame 102 is illustrated as having linear or long curved members, it will be appreciated that the support frame 102 and/or the cross-members 120 can have a configuration that allows the support frame 102 and/or the cross-members 120 to be flexible. Examples of such configurations include those that are zigzag and/or serpentine so as to allow the frame to be radially compressible. As such, the present invention should not be limited to the illustration of the support frame 102.

The support frame 102 can also provide sufficient contact and expansion force with the surface of a body lumen wall to encourage fixation of the valve 100 and to prevent retrograde flow within the body lumen. Anchoring elements (e.g., barbs) can also be included with valve 100, as will be discussed herein.

The members (e.g., first end member 110 and a second end member 112, cross-members 120) forming support frame 102 can include a variety of cross-sectional shapes and dimensions. For example, cross-sectional shapes for the members 122 can include, but are not limited to, circular, tubular, I-shaped, T-shaped, oval, and triangular. The members can also have a single cross-sectional shape (e.g., all members of support frame 102 can have a circular cross-sectional shape). In an additional embodiment, the members of the support frame 102 can include two or more cross-sectional shapes (e.g., a first cross-sectional shape for both the first end member 110 and a second end member 112, and a second cross-sectional shape for the cross-members 120).

The support frame 102 can be formed from any number of materials. For example, the support frame 102 can be formed from a biocompatible metal, metal alloy, polymeric material, or combination thereof. As discussed herein, the support frame 102 can be self-expanding or balloon expandable. Examples of suitable materials for the support frame 102 include, but are not limited to, medical grade stainless steel (e.g., 316L), titanium, tantalum, platinum alloys, niobium alloys, cobalt alloys, alginate, or combinations thereof. In an additional embodiment, the support frame 102 may be formed from a shape-memory material, such as shape memory plastics, polymers, and thermoplastic materials which are inert in the body. Shaped memory alloys having superelastic properties generally made from specific ratios of nickel and titanium, commonly known as nitinol, are also possible materials. Other materials are also possible.

Members (e.g., first end member 110 and a second end member 112, cross-members 120) of the support frame 102 can be shaped and joined in any number of ways. For example, a single contiguous member can be bent around an elongate tubular mandrel to form the end members 110 and 112 of the support frame 102. The free ends of the single contiguous member can then be welded, fused, crimped, or otherwise joined together to form the support frame 102. In an additional embodiment, the cross-members 120 can be joined to the end members 110 and 112 in a similar manner. Alternatively, the support frame 102 can be derived (e.g., laser cut, water cut) from a single tubular segment. The support frame 102 can be heat set by a method as is typically known for the material which forms the support frame 102.

Support frame 102 and cover 104 can be expanded to provide lumen 126 having any number of sizes. For example, the size of lumen 126 can be determined based upon the type of body lumen and the body lumen size in which the valve 100 is to be placed. In an additional example, there can also be a minimum value for the width 128 for the support frame 102 that ensures that the support frame 102 will have an appropriate expansion force against the inner wall of the body lumen in which the valve 100 is being placed. The support frame 102 can also include a longitudinal length 130.

In one embodiment, the support frame 102 can further include one or more anchoring elements. For example, the one or more anchoring elements can include, but are not limited to, one or more barbs 132 projecting from the outer surface 106 of the support frame 102. The valve 100 can further include one or more radiopaque markers (e.g., tabs, sleeves, welds). For example, one or more portions of the valve frame 102 can be formed from a radiopaque material. Radiopaque markers can be attached to and/or coated onto one or more locations along the support frame 102. Examples of radiopaque material include, but are not limited to, gold, tantalum, and platinum. The position of the one or more radiopaque markers can be selected so as to provide information on the position, location and orientation of the valve 100 during its implantation.

As discussed herein, the cover 104 of the cardiac valve 100 forms valve leaflets 133 having surfaces defining a reversibly sealable opening 134 for unidirectional flow of a liquid through the valve 100. For example, the cover 104 can extend across an area between the convex curves 116 and the concave curves 118 of the second end member 112 to form valve leaflets 133 of the cardiac valve 100. The position and number of the convex and concave curves 116 and 118 in the second end member 112 determine the number of valve leaflets 133 of the cardiac valve 100.

For example, FIGS. 1A and 1B provide a bi-leaflet cardiac valve according to an embodiment of the present invention. As illustrated in FIGS. 1A and 1B, cover 104 extends across the area between a first convex curve 136 and a second convex curve 138 and down to the concave curves 118 of the second end member 112 to form a first valve leaflet 140 and a second valve leaflet 142.

In one embodiment, the first convex curve 136 and the second convex curve 138 of the second end member 112 are positioned opposite each other along a common axis 144. In this example, the common axis 144 bisects support frame 102 into symmetrical portions. As a result, the first valve leaflet 140 and the second valve leaflet 142 each display substantially the same shape, size and configuration as each other. In an alternative embodiment, the first convex curve 136 and the second convex curve 138 can be positioned so that the common axis 144 divides the support frame 102 into non-symmetrical portions. In this embodiment, the first valve leaflet 140 and the second valve leaflet 142 can have different shapes, sizes and configurations relative to each other.

In an additional embodiment, the cover 104 also extends over the first end member 110. In contrast to the second end member 112, however, the cover 104 terminates along the convex and concave curves 116 and 118 of the first end member 110 so as to define an open area 146 between the sequence of convex curves 116 and concave curves 118. As will be more fully discussed below, providing the open area 146 allows the valve 100 to accommodate the anatomical structures of the autologous valve being replaced so as to reduce any potential interference with anatomical structures adjacent the autologous valve (e.g., the coronary ostia located adjacent aortic valve).

Although the embodiments in FIGS. 1A-1D illustrate and describe a bi-leaflet configuration for the valve 100 of the present invention, designs employing a different number of valve leaflets are possible. For example, the second end member 112 can include additional convex curves 116 and the concave curves 118 so as to provide support structures for additional valve leaflets 133 (e.g., a tri-leaflet valve).

The cover 104 in conjunction with the support frame 102 defines the lumen 126 of the cardiac valve 100 for passing fluid (e.g., blood) there-through. The cover 104 further includes surfaces defining a reversibly sealable opening 134 for unidirectional flow of a liquid through the lumen 126. For example, a portion of the first valve leaflet 140 and the second valve leaflet 142 can join to form the reversibly sealable opening 134 for unidirectional flow of a liquid through the cardiac valve 100. FIGS. 1A and 1B illustrate embodiments in which the surfaces of the cover 104 can be deflectable between a closed configuration (FIG. 1B) in which fluid flow through the lumen 126 can be restricted and an open configuration (FIG. 1A) in which fluid flow through the lumen 126 can be permitted.

The first valve leaflet 140 and the second valve leaflet 142 can move relative the support frame 102 (i.e., the first valve leaflet 140 and the second valve leaflet 142 are attached to and pivot along the support frame 102). In one embodiment, the cover 104 provides sufficient excess material spanning support frame 102 to allow the first valve leaflet 140 and the second valve leaflet 142 to join sealing surfaces 148 at the reversibly sealable opening 134. The reversibly sealable opening 134 formed by the first and second valve leaflets 140 and 142 opens and closes in response to the fluid pressure differential across the valve leaflets 140 and 142. That is, antegrade blood flow causes the valve leaflets to open, thereby providing for unidirectional blood flow through the reversibly sealable opening. In contrast, retrograde blood flow causes the valve leaflets close, thereby preventing blood flow from passing through the reversibly sealable opening.

The first valve leaflet 140 and the second valve leaflet 142 further include arcuate edges 150 and 152 that are positioned adjacent each other along a substantially catenary curve between the first convex curve 136 and the second convex curve 138 of the second end member 112 in the closed configuration (FIG. 1B) of valve 100. Similarly, arcuate edges 150 and 152 can form the reversibly sealable opening 134 when the valve 100 is in the open configuration (FIG. 1A).

For example, under antegrade fluid flow (i.e., positive fluid pressure) moving from the first end member 110 towards the second end member 112 of the valve 100, the first and second valve leaflets 140 and 142 can expand toward the support frame 102 to create an opening through which fluid is permitted to move. In one embodiment, the first valve leaflet 140 and the second valve leaflet 142 can each expand to form a semi-tubular structure when fluid opens the reversibly sealable opening 134. In an additional embodiment, arcuate edge 150 and 152 of valve 100 can open to approximately the full inner diameter of a body lumen. An example of the open configuration for the valve is shown in FIG. 1A.

Under a retrograde fluid flow (i.e., negative fluid pressure) moving from the second end member 112 towards the first end member 110, the first and second valve leaflets 140 and 142 move away from the support frame 102 as the valve leaflets 140 and 142 begin to close. In one embodiment, the valve leaflets 140 and 142 include a predefined shape that allows for the retrograde fluid flow to develop pressure on a major surface 154 of the first and second valve leaflets 140 and 142.

For example, the major surface 154 can have a concave shape 156 to better collect retrograde fluid flow to urge the first valve leaflet 140 and the second valve leaflet 142 towards the closed configuration. As fluid pressure builds, the first and second valve leaflets 140 and 142 move towards each other eventually forming the reversibly sealable opening 134 (i.e., closing the valve 100), thereby restricting retrograde fluid flow through the valve 100.

In an additional embodiment, the first valve leaflet 140 and the second valve leaflet 142 can include one or more support structures, where the support structures can be integrated into and/or onto the valve leaflets 140 and 142. For example, the first valve leaflet 140 and the second valve leaflet 142 can include one or more support ribs having a predetermined shape. In one embodiment, the predetermined shape of the support ribs can include a curved bias so as to provide the first valve leaflet 140 and the second valve leaflet 142 with a curved configuration. Support ribs can be constructed of a flexible material and have dimensions (e.g., thickness, width and length) and cross-sectional shape that allows the support ribs to be flexible when the first valve leaflet 140 and the second valve leaflet 142 are urged into an open position upon experiencing sufficient blood flow pressure from the direction upstream from the valve, e.g., antegrade blood flow, and stiff when the first valve leaflet 140 and the second valve leaflet 142 are urged into a closed position upon experiencing sufficient back flow pressure from the direction downstream from the valve, e.g., retrograde blood flow. In an additional embodiment, support ribs can also be attached to support frame 102 so as to impart a spring bias to the valve leaflets 133 in either the open or the closed configuration.

In one embodiment, cover 104 used to form the valve leaflets 140 and 142 can be constructed of a material sufficiently thin and pliable so as to permit radially-collapsing of the valve leaflets for delivery by catheter to a location within a body lumen. The cover 104 can be constructed of a biocompatible material that can be either synthetic or biologic or a combination of synthetic and biologic biocompatible material. Possible synthetic materials include, but are not limited to, expanded polytetrafluoroethylene (ePTFE), polytetrafluoroethylene (PTFE), polystyrene-polyisobutylene-polystyrene (SIBS), polyurethane, segmented poly(carbonate-urethane), polyester, polyethlylene (PE), polyethylene terephthalate (PET), silk, urethane, Rayon, Silicone, or the like. In an additional embodiment, the synthetic material can also include metals, such as stainless steel (e.g., 316L) and nitinol. These synthetic materials can be in a woven, a knit, a cast or other known physical fluid-impermeable or permeable configurations.

Possible biologic materials include, but are not limited to, autologous, allogeneic or xenograft material. These include explanted veins, pericardium, facia lata, harvested cardiac valves, bladder, vein wall, various collagen types, elastin, intestinal submucosa, and decellularized basement membrane materials, such as small intestine submucosa (SIS), amniotic tissue, or umbilical vein.

As discussed herein, the cover 104 can be located over at least the outer surface 106 of the support frame 102. FIGS. 1A-1D provide one illustration of this embodiment. In an additional embodiment, the cover 104 can be located over at least the inner surface 108 of the support frame 102.

FIGS. 2A-2B provide a cross-sectional perspective view of cover 204 extending over both an inner surface 208 and the outer surface 206 of the support frame 202 to form the bi-leaflet cardiac valve. In one example, the cover 204 can further be located over the openings 224 defined by the members of the support frame 202. The cover 204 can also be joined to itself through the openings 224 so as to fully or partially encase the support frame 202.

Numerous techniques may be employed to laminate or bond the cover 204 on the outer surface 206 and/or the inner surface 208 of the support frame 202, including heat setting, adhesive welding, interlocking, application of uniform force and other bonding techniques. Additionally, the cover 204 may be folded over the first end member 210 of the support frame 202 to provide the cover 204 on both the outer surface 206 and the inner surface 208. Cover 204 can also be joined to itself and/or the members according to the methods described in U.S. Patent Application Publication US 2002/0178570 to Sogard et al.

The valve 200 can further include a layer of material 258 positioned between the cover 204 extending over the inner surface 208 and the outer surface 206 of the support frame 202. The layer of material 258 can be formed from the biocompatible material used for the cover 204. The layer of material 258, however, can be structurally different than the material of cover 204. For example, cover 204 can include a fluid permeable open woven, or knit, physical configuration to allow for tissue in-growth and stabilization, whereas the layer of material 258 can have a fluid impermeable physical configuration. Examples of the material 258 include, but are not limited to, the synthetic materials described herein. Other combinations of physical configurations for the cover 204 and the layer of material 258 are also possible.

Referring again to FIGS. 1A-1D, the support frame 102 and/or the cover 104, including the valve leaflets 140 and 142, may also be treated and/or coated with any number of surface or material treatments. For example, suitable bioactive agents which may be incorporated with or utilized together with the present invention may be selected from silver antimicrobial agents, metallic antimicrobial materials, growth factors, cellular migration agents, cellular proliferation agents, anti-coagulant substances, stenosis inhibitors, thrombo-resistant agents, antibiotic agents, anti-tumor agents, anti-proliferative agents, growth hormones, antiviral agents, anti-angiogenic agents, angiogenic agents, cholesterol-lowering agents, vasodilating agents, agents that interfere with endogenous vasoactive mechanisms, hormones, their homologs, derivatives, fragments, pharmaceutical salts and combinations thereof.

In the various embodiments of the present invention, the most useful bioactive agents can include those that modulate thrombosis, those that encourage cellular ingrowth, through-growth, and endothelialization, those that resist infection, and those that reduce calcification. For example, coating treatments can include one or more biologically active compounds and/or materials that may promote and/or inhibit endothelial, smooth muscle, fibroblast, and/or other cellular growth onto or into the support frame 102 and/or the cover 104, including the valve leaflets 140 and 142. Examples of such coatings include, but are not limited to, polyglactic acid, poly-L-lactic acid, glycol-compounds, and lipid compounds. Additionally, coatings can include medications, genetic agents, chemical agents, and/or other materials and additives. In addition, in embodiments having tubular members such as the tubular member 482 illustrated in FIGS. 4A-4B, agents that limit or decrease cellular proliferation can be useful. Similarly, the support frame 102 and/or the cover 104 may be seeded and covered with cultured tissue cells (e.g., endothelial cells) derived from a either a donor or the host patient which are attached to the valve leaflets 140 and 142. The cultured tissue cells may be initially positioned to extend either partially or fully over the valve leaflets 140 and 142.

Cover 104, in addition to forming valve leaflets 140 and 142, can also be capable of inhibiting thrombus formation, as discussed herein. Additionally, cover 104 may either prevent or facilitate tissue ingrowth there-through, as the particular application for the valve 100 may dictate. For example, cover 104 on the outer surface 106 may be formed from a porous material to facilitate tissue ingrowth there-through, while cover 104 on the inner surface 108 may be formed from a material or a treated material which inhibits tissue ingrowth.

Cells can be associated with the present invention. For example, cells that have been genetically engineered to deliver bioactive proteins, such as the growth factors or antibodies mentioned herein, to the implant site can be associated with the present invention. Cells can be of human origin (autologous or allogenic) or from an animal source (xenogenic). Cells can be pre-treated with medication or pre-processed such as by sorting or encapsulation. The delivery media can be formulated as needed to maintain cell function and viability.

Thrombo-resistant agents associated with the valve may be selected from, but not limited to, heparin, heparin sulfate, hirudin, hyaluronic acid, chondroitin sulfate, dermatan sulfate, keratin sulfate, PPack (detropyenylalanine praline arginine chloromethylketone), lytic agents, including urokinase and streptokinase, their homologs, analogs, fragments, derivatives and pharmaceutical salts thereof.

Anti-coagulants can include, but are not limited to, D-Phe-Pro-Arg chloromethyl ketone, an RGD peptide-containing compound, heparain, antithrombin compounds, platelet receptor antagonists, anti-thrombin antibodies, anti-platelet receptor antibodies, aspirin, prostaglandin inhibitors, platelet inhibitors, tick antiplatelet peptides and combinations thereof.

Antibiotic agents can include, but are not limited to, penicillins, cephalosportins, vancomycins, aminoglycosides, quinolonges, polymyxins, erythromycins, tetracyclines, chloraphenicols, clindamycins, lincomycins, sulfonamides, their homologs, analogs, derivatives, pharmaceutical salts and combinations thereof.

Anti-proliferative agents for use in the present invention can include, but are not limited to, the following: paclitaxel, sirolimus, everolimus, or monoclonal antibodies capable of blocking smooth muscle cell proliferation, related compounds, derivatives, and combinations thereof.

Vascular cell growth inhibitors can include, but are not limited to, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of a an antibody and a cytotoxin.

Vascular cell growth promoters include, but are not limited to, transcriptional activators and transcriptional promoters. Anti-inflammatory agents can include, but are not limited to, dexametbasone, prednisolone, corticosterone, budesonide, estrogen, sulfasalazinemesalamne, and combinations thereof.

Figure 3A:
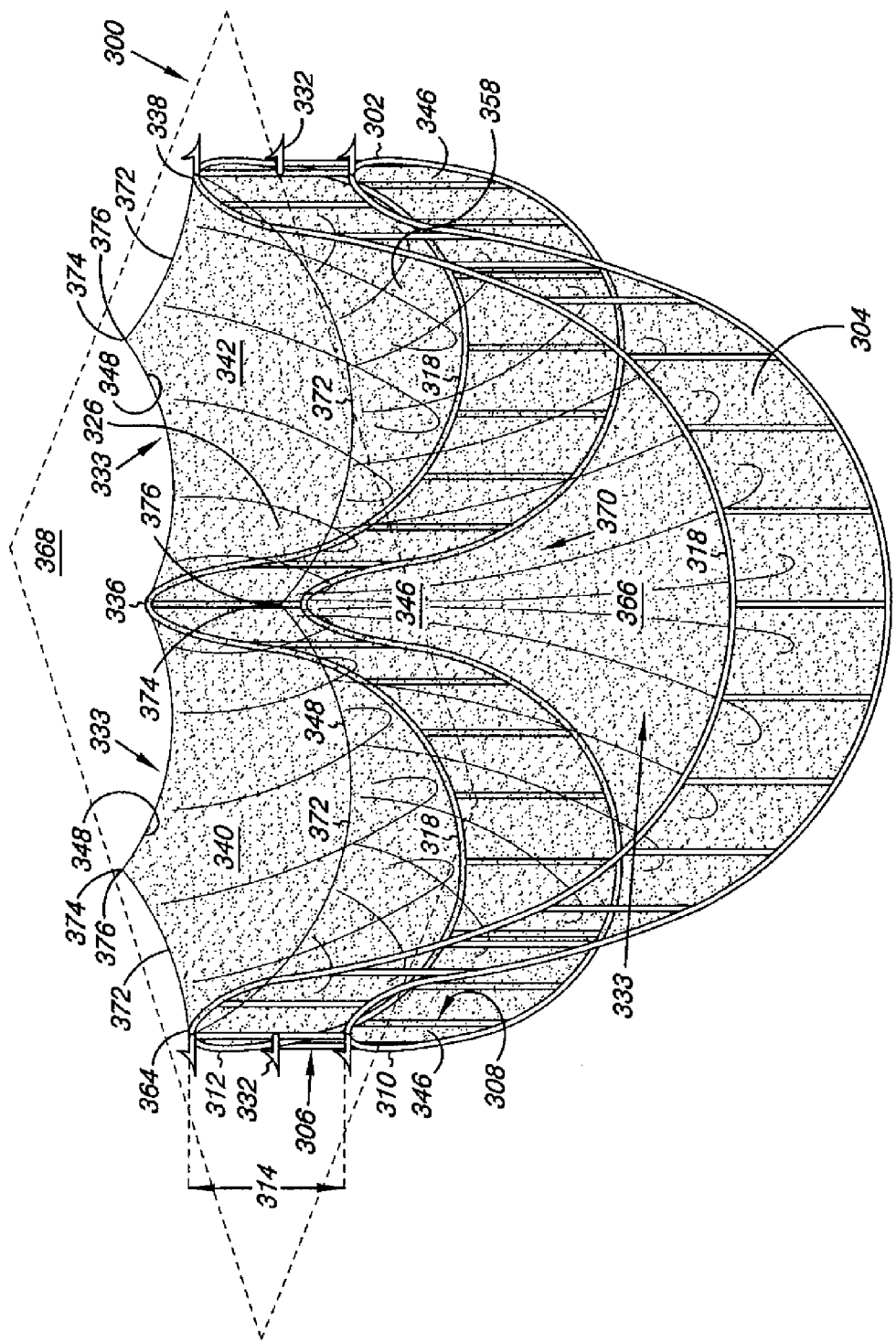
FIGS. 3A and 3B illustrate another embodiment of a valve in perspective view.
Figure 3B:
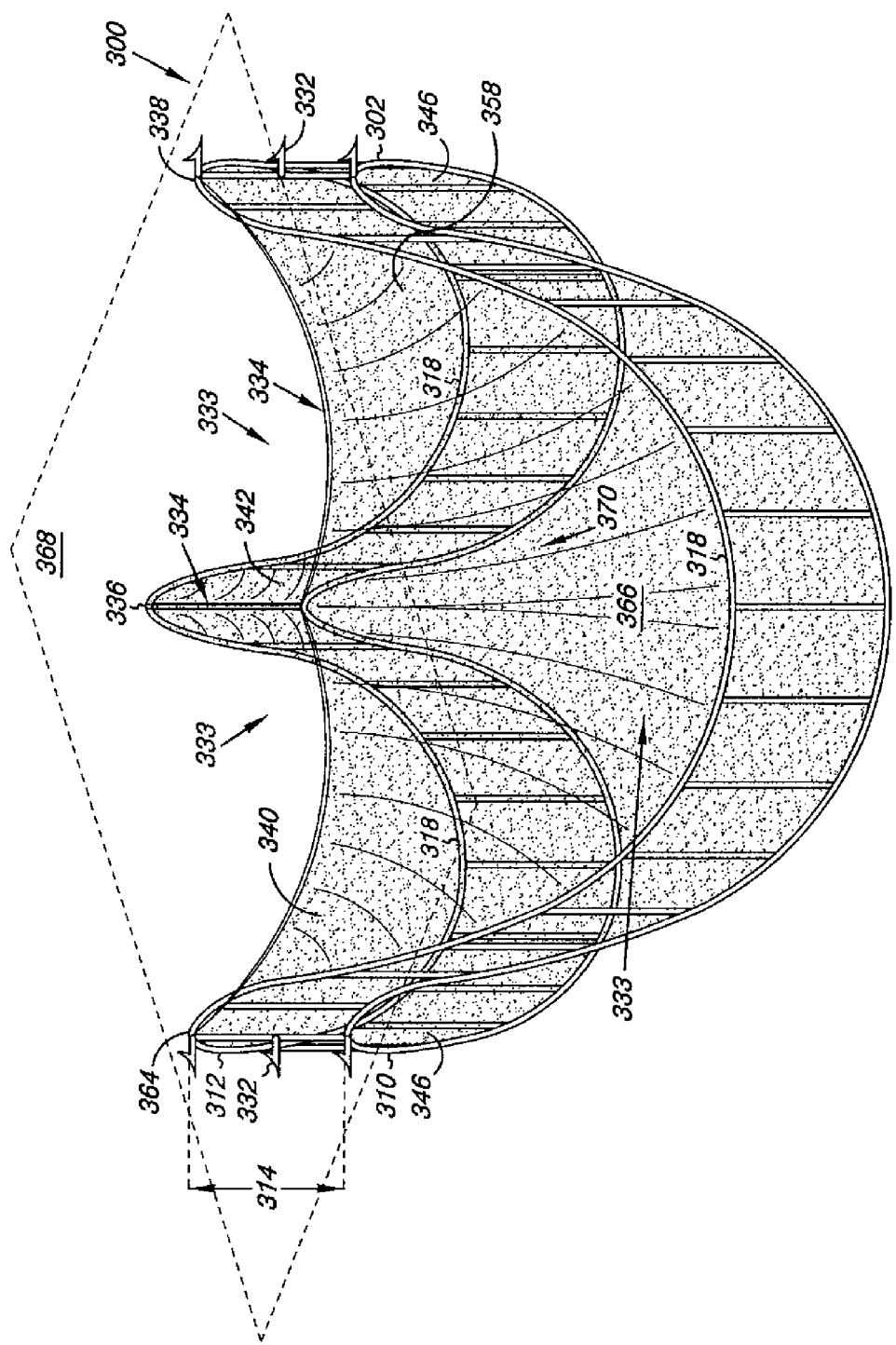

FIGS. 3A and 3B illustrate an additional embodiment of a cardiac valve 300. FIGS. 3A and 3B provide a perspective illustration of valve 300 having three valve leaflets 333 in an open configuration (FIG. 3A) and a closed configuration (FIG. 3B).

As discussed herein, cardiac valve 300 includes the support frame 302 having the first end member 310 and the second end member 312 opposing the first end member 310 in the substantially fixed distance relationship 314. In the present example, the cover 304 of the cardiac valve 300 forms a tri-leaflet valve having surfaces defining the reversibly sealable opening 334 for unidirectional flow of a liquid through the valve 300. As illustrated, FIGS. 3A and 3B provide a tri-leaflet cardiac valve in which cover 304 extends across the area between the first convex curve 336, the second convex curve 338, and a third convex curve 364, and down to the concave curves 118 of the second end member 112 to form the first valve leaflet 340, the second valve leaflet 342, and a third valve leaflet 366

In one embodiment, the convex curves 336, 338, and 364 can lay on a common plane 368, as illustrated in FIGS. 3A and 3B. However, the convex curves 336, 338, and 364 can lay need not all lay on the common plane 368. It is possible that one or more of the convex curves 336, 338, and 364 can lie above and/or below the common plane 368. In addition, the convex curves 336, 338, and 364 can be positioned at equal distances around the second end member 312. As a result, the valve leaflets 336, 338, and 364 each display substantially the same shape, size and configuration as each other. In an alternative embodiment, the convex curves 336, 338, and 364 can be positioned at one or more unequal distances around the second end member 312. In this embodiment, the valve leaflets 336, 338, and 364 can each have different shapes, sizes and configurations relative to each other.

The cover 304 in conjunction with the support frame 302 defines the lumen 326 of the cardiac valve 300 for passing fluid (e.g., blood) there-through. The cover 304 can further include surfaces defining the reversibly sealable opening 334 for unidirectional flow of a liquid through the lumen 326. For example, a portion of the first valve leaflet 340, the second valve leaflet 342, and the third valve leaflet 366 can join to form the reversibly sealable opening 334 for unidirectional flow of a liquid through the cardiac valve 300. FIGS. 3A and 3B illustrate embodiments in which the valve leaflets 340, 342, and 366 can deflect between a closed configuration (FIG. 3B) in which fluid flow through the lumen 326 can be restricted and an open configuration (FIG. 3A) in which fluid flow through the lumen 326 can be permitted.

The first valve leaflet 340, the second valve leaflet 342, and the third valve leaflet 366 can move relative the support frame 302 between the open configuration and the closed configuration. As discussed, the cover 304 provides sufficient excess material spanning support frame 302 to allow the valve leaflets 340, 342, and 366 to join sealing surfaces 348 at a reversibly sealable opening 334. The reversibly sealable opening 334 formed by the first, second, and third valve leaflets 340, 342, and 366 opens and closes in response to the fluid pressure differential across the valve leaflets.

The valve leaflets 340, 342, and 366 each include concave surfaces 370 projecting from the support frame 302 towards an arcuate edge 372 projecting into the lumen 326. As discussed, the valve leaflets 340, 342, and 366 can have approximately the same size and shape. The arcuate edge 372 of the valve leaflets 340, 342, and 366 can each further include a nodular interruption 374 at approximately the center 376 of the arcuate edge 372 to allow the edges of the leaflets 340, 342, and 366 to properly meet as the valve closes.

During retrograde flow (i.e., negative fluid pressure), the valve leaflets 340, 342, and 366 can fall into the lumen to close the reversibly sealable opening 334 and support the column of fluid (e.g., blood). During antegrade fluid flow (i.e., positive fluid pressure) the valve leaflets 340, 342, and 366 can expand or move toward the support frame 302 to create an opening through which fluid is permitted to move. In one embodiment, the valve leaflets 340, 342, and 366 can each expand or move to form a semi-tubular structure when fluid opens the reversibly sealable opening 334. In an additional embodiment, the valve leaflets 340, 342, and 366 can include one or more support structures (e.g., support ribs), as discussed herein.

Cover 304 can extend over at least the outer surface 306 of the support frame 302 to form the valve leaflets of the tri-leaflet cardiac valve. Alternatively, cover 304 can also be located over at least the inner surface 308 of the support frame 302 to form the valve leaflets of the tri-leaflet cardiac valve. The cover 304 can be joined to the support frame 302 and itself as discussed herein. In addition, the valve 300 can further include a layer of material 358 positioned between the cover 304 extending over the inner surface 308 and the outer surface 306 of the support frame 302. The cover 304, including the valve leaflets 340, 342, and 366, may also be treated and/or coated with any number of surface or material treatments, as discussed herein.

Figure 4A:
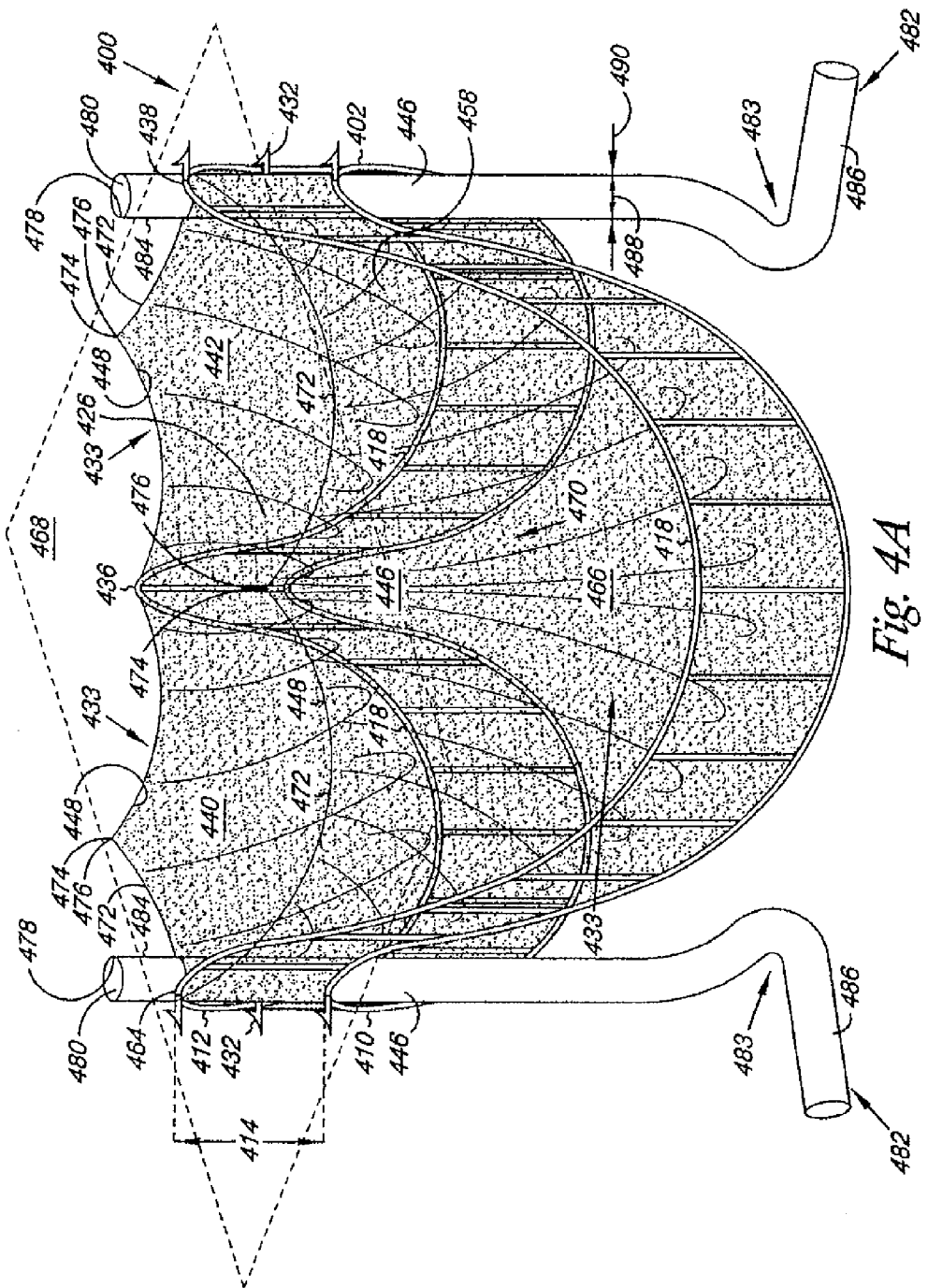
FIGS. 4A and 4B illustrate another embodiment of a valve in perspective view.
Figure 4B:
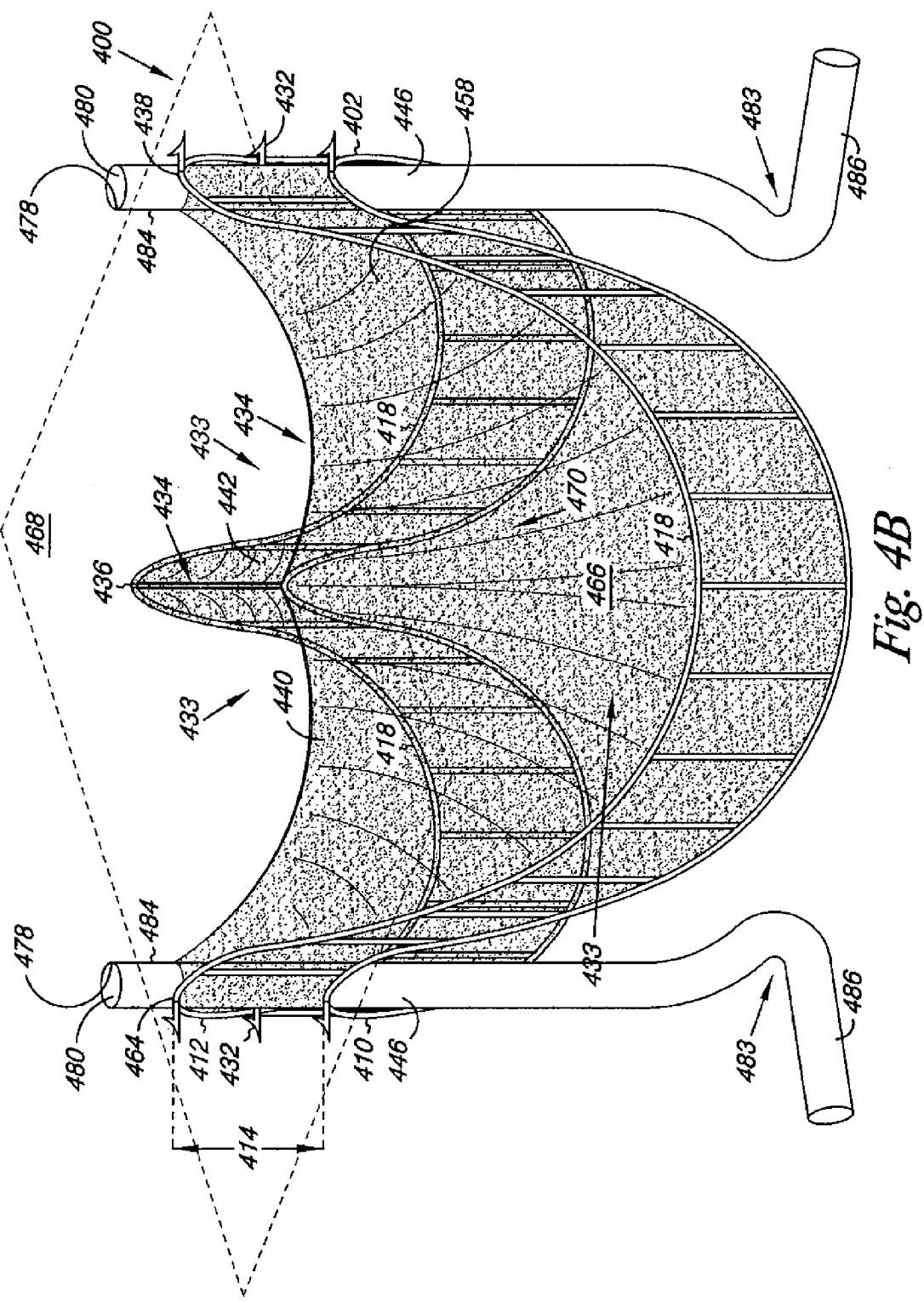

FIGS. 4A and 4B illustrate a further embodiment of a cardiac valve 400. FIGS. 4A and 4B provide a perspective illustration of valve 400 in an open configuration (FIG. 4A) and a closed configuration (FIG. 4B). As discussed herein, the valve 400 the support frame 402 and the cover 404 that forms valve leaflets having surfaces defining a reversibly sealable opening 434 for unidirectional flow of a liquid through the valve 400.

In addition, the present embodiment further includes an elongate tubular member 482 having a first end 484 and a second end 486. As illustrated, the elongate tubular member 482 can be positioned relative the support frame 402 to allow the first end 484 of the member 482 to be on a first side of the valve leaflets and the second end 486 on a second side of the valve leaflets. In one embodiment, the tubular member 482 can pass through an opening in a valve leaflet, where the tubular member 482 and the valve leaflet form a fluid tight seal. Alternatively, the tubular member 482 passes through a region of the reversibly sealable opening 434, where the leaflets seal around the tubular member 482 when they are in their closed position. As illustrated in FIGS. 4A and 4B, the tubular member 482 can be positioned within the opening defined by the support frame 402. In an alternative embodiment, the tubular member 482 can be positioned outside of the support frame 402.

The tubular member 482 can allow fluid communication across the valve 400 when the valve leaflet 433 are in their closed position. In one embodiment, the tubular member 482 can allow for blood at an arterial pressure to be supplied from a region distal to the valve 400 to vessels located proximal the valve 400. In one embodiment, the tubular member 482 can allow the valve 400 to be positioned at a more convenient and/or less-diseased location in the vasculature (e.g., the aorta) while still allowing blood at arterial pressure to be supplied to the appropriate coronary arteries (e.g., via the coronary ostium).

The tubular member 482 can include any number of physical configurations. For example, as shown in FIG. 4A, the tubular member 482 can include a predetermined length and a predetermined bend 483 to allow the second end 486 of the tubular member 482 to be implanted in a desired location. Examples of such locations include, but are not limited to, a coronary ostium. The predetermined length of the tubular member 482 can be in a range from 10 mm to 50 mm, where the length of the tubular member 482 will be determined based on where the valve 400 is being implanted along with the patient's individual physiological parameters and measurements.

As will be appreciated, the valve 400 can include more than one tubular member 482. For example, the valve 400 can include two or more tubular members 482, each tubular member supplying a coronary artery of the patient's vasculature. In addition, each of the tubular members 482 can have similar or distinct physical characteristics (e.g., length, inner/outer diameter, predetermined shape). In one embodiment, each of the tubular members 482 can further include one or more radiopaque marks to allow each tubular member 482 to be uniquely identified.

The tubular member 482 can further include a predetermined shape. In one embodiment, the predetermined shape can be determined by the anatomical location in which the valve 400 is being placed along with the anatomical location in which the second end 486 of the tubular member 482 is to be placed. As illustrated in FIGS. 4A and 4B, the tubular member 482 can include combinations of linear and bend portions imparted into the tubular member 484 (e.g., the predetermined bend 483 illustrated in FIG. 4B).

The tubular member 482 can be constructed of a material having sufficient flexibility so as to permit the second end 486 of the tubular member 482 to remain positioned in its proper anatomical location within the patient, while also being flexible enough to allow the first end 484 to move radially with the valve leaflet. The tubular member 482 can be constructed of a biocompatible material that can be either synthetic or biologic. Examples of these materials include those discussed herein for the cover 404. In addition, the material used in the construction of the tubular member 484 can be the same or a different material used for the construction of the cover 404. The tubular member 482 can also include a stent support structure to help maintain a predetermined shape of the tubular member 482.

The tubular member 482 further includes an inner diameter 488 and outer diameter 490. The inner diameter 488 can be in a range of 2.0 mm to 5.5 mm. Alternatively, the inner diameter 488 can be in a range of 3.0 mm to 4.5 mm. In one embodiment, the dimension of the inner diameter 488 will typically be a function of the volume of fluid flow that is desired to move through the tubular member 484. The dimension for the outer diameter 490 will be dependent upon the wall thickness of the tubular member 482 required to provide proper flexibility and rigidity to maintain its position once placed in the patient.

The embodiments of the valve of the present invention can be formed in any number of ways. For example, a support frame and a cover are both provided for forming the cardiac valve. In the present example, the cover can have a cylindrical shape of essentially uniform inner diameter, where the inner diameter of the cover is approximately the same size as an outer diameter of the support frame.

The cover can be positioned over the outer surface of the support frame. For example, the cover can be stretched slightly to allow the support frame to be placed within the cover. Alternatively, the outer diameter of the tubular frame could be enlarged so as to place the cover around the outer surface of the support frame. Other ways of placing the cover around the outer surface of the support frame are also possible, including placing the cover around both the inside and the outside of the frame.

In one embodiment, the cover can be positioned over and attached to the support frame so that the cover extends between the convex curves of the second end member to form the valve leaflets. For example, the support frame includes the first convex curve and the second convex curve along the second end member. Providing cover over the support frame then forms the first valve leaflet and the second valve leaflet of the cardiac valve.

As discussed herein, the cover can also be trimmed along the first end member so as to define the open area between the sequence of convex curves and concave curves along the first end member. Alternatively, the cover can include a first end having a series of convex and concave curves that correspond to those of the first end member so as to provide the open area.

In an additional embodiment, the cardiac valve can be formed by providing support frame and cover, where the second end member of support frame includes the first convex curve, the second convex curve, and the third convex curve. Cover can include cylindrical shape that has a second end having a predetermined shape that allows for the formation of the valve leaflets of the tri-leaflet cardiac valve. The second end can also include arcuate edges each having the optional nodular interruption. The cover further includes concave surfaces, as described herein, which can be imparted into the cover through any number of manufacturing processes, including, but not limited to, thermo-molding, heat setting, and chemical cross-linking. As discussed herein, this example of the cover permits the valve leaflets to be created once the cover is properly positioned on the support frame.

As discussed herein, the cover can also be positioned over both the outer surface and the inner surface of the support frame. For example, two covers can be positioned on the support frame to provide an embodiment of the cardiac valve, or a longer cover can be used over the support frame. In addition, additional material can be positioned between the two covers at least in the area between the convex and concave curves of the second end member.

In addition, one or more flexible support ribs having a predetermined shape could also be incorporated into the cover in forming the concave surfaces. As discussed herein, the cover configuration having the arcuate edges, nodular interruptions, and the concave surfaces permits the valve leaflets to be created once the cover is properly positioned over the support frame. The cover can then be affixed to the support frame and itself as discussed herein.

The cover can also be trimmed along the first end member so as to define the open area between the sequence of convex curves and concave curves along the first end member. Alternatively, the first end of cover can include a series of convex and concave curves that correspond to those of the first end member so as to provide the open area.

In an additional embodiment, surfaces defining the opening through or around the cover can also be provided on the cardiac valve. The tubular member can then be coupled in fluid tight communication to the opening to provide fluid communication with the opening around or through the cover. In one embodiment, the first end of the tubular member can be coupled to the support frame with the opening and the lumen of the tubular member aligned so that fluid can move through the opening and the tubular member once the valve has been implanted in a patient. Alternatively, the tubular member can be positioned in the patient, independent of the valve and then subsequently coupled to the valve once the valve has been implanted in the patient.

As discussed herein, the tubular member allows for the valve to be positioned in any number of locations within the vasculature while still allowing fluid communication with adjacent physiological structures. For example, valve could be implanted in the aorta of a patient downstream of the coronary ostia. In order to provide sufficient blood supply to the coronary ostia, the tubular member can be positioned with the second end of the tubular member in the coronary ostia so as to supply arterial blood at arterial pressures to the coronary arteries.

Figure 5:
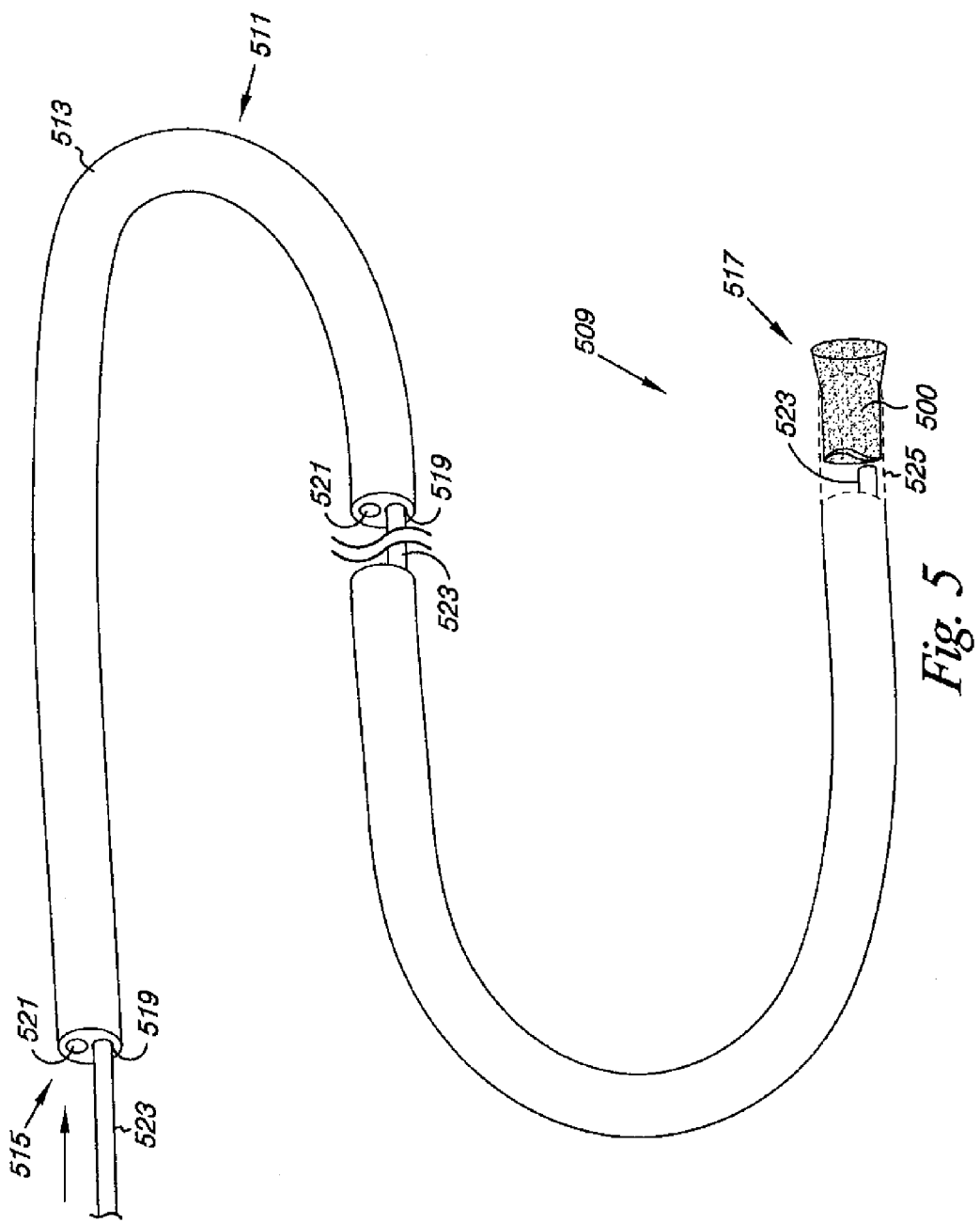
FIG. 5 illustrates an embodiment of a system that includes a valve.

FIG. 5 illustrates one embodiment of a system 509. System 509 includes valve 500, as described herein, reversibly joined to a delivery catheter 511. The delivery catheter 511 includes an elongate body 513 having a proximal end 515 and a distal end 517, where valve 500 can be located between the proximal end 515 and distal end 517. The delivery catheter 511 can further include a lumen 519 longitudinally extending to the distal end 517. In one embodiment, lumen 519 extends between proximal end 515 and distal end 517 of catheter 511. The catheter 511 can further include a guidewire lumen 521 that extends within the elongate body 513, were the guidewire lumen 521 can receive a guidewire for positioning the catheter 511 and the valve 500 within a body lumen (e.g., the aorta of a patient).

The system 509 can further include a deployment shaft 523 positioned within lumen 519, and a sheath 525 positioned adjacent the distal end 517. In one embodiment, the valve 500 can be positioned at least partially within the sheath 525 and adjacent the deployment shaft 523. The deployment shaft 523 can be moved within the lumen 519 to deploy valve 500. For example, deployment shaft 523 can be used to push valve 500 from sheath 525 in deploying valve 500.

Figure 6:
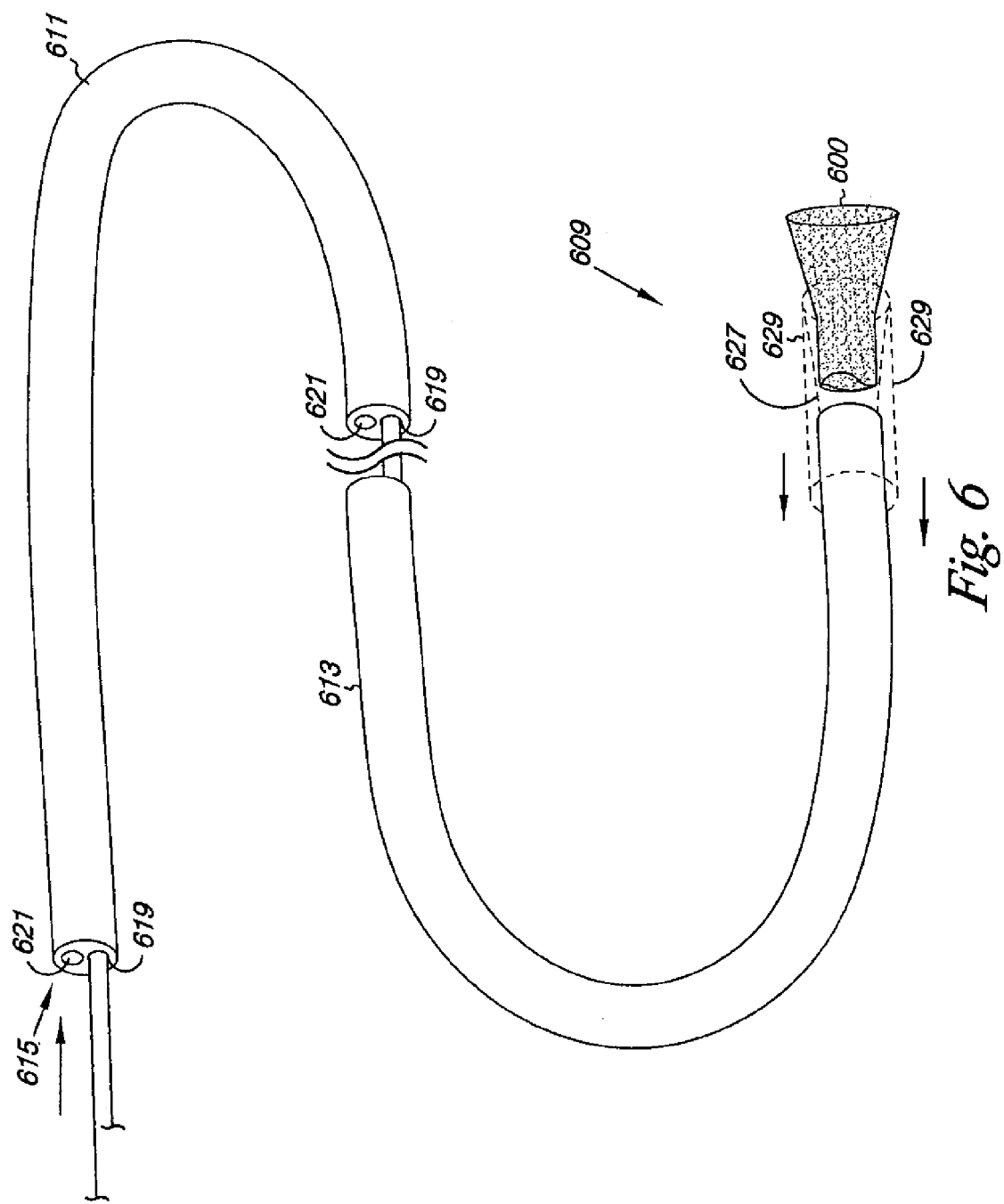
FIG. 6 illustrates an embodiment of a system that includes a valve.

FIG. 6 illustrates an additional embodiment of the system 609. The catheter 611 includes elongate body 613, lumen 619, a retraction system 627 and a retractable sheath 629. The retractable sheath 629 can be positioned over at least a portion of the elongate body 613, where the retractable sheath 629 can move longitudinally along the elongate body 613. The valve 600 can be positioned at least partially within the retractable sheath 629, where the retractable sheath 629 moves along the elongate body 613 to deploy the valve 600. In one embodiment, retraction system 627 includes one or more wires 699 coupled to the retractable sheath 627, where the wires 699 are positioned at least partially within and extend through lumen 619 in the elongate body 613. Wires 699 of the retraction system 627 can then be used to retract the retractable sheath 629 in deploying valve 600.

Figure 7:
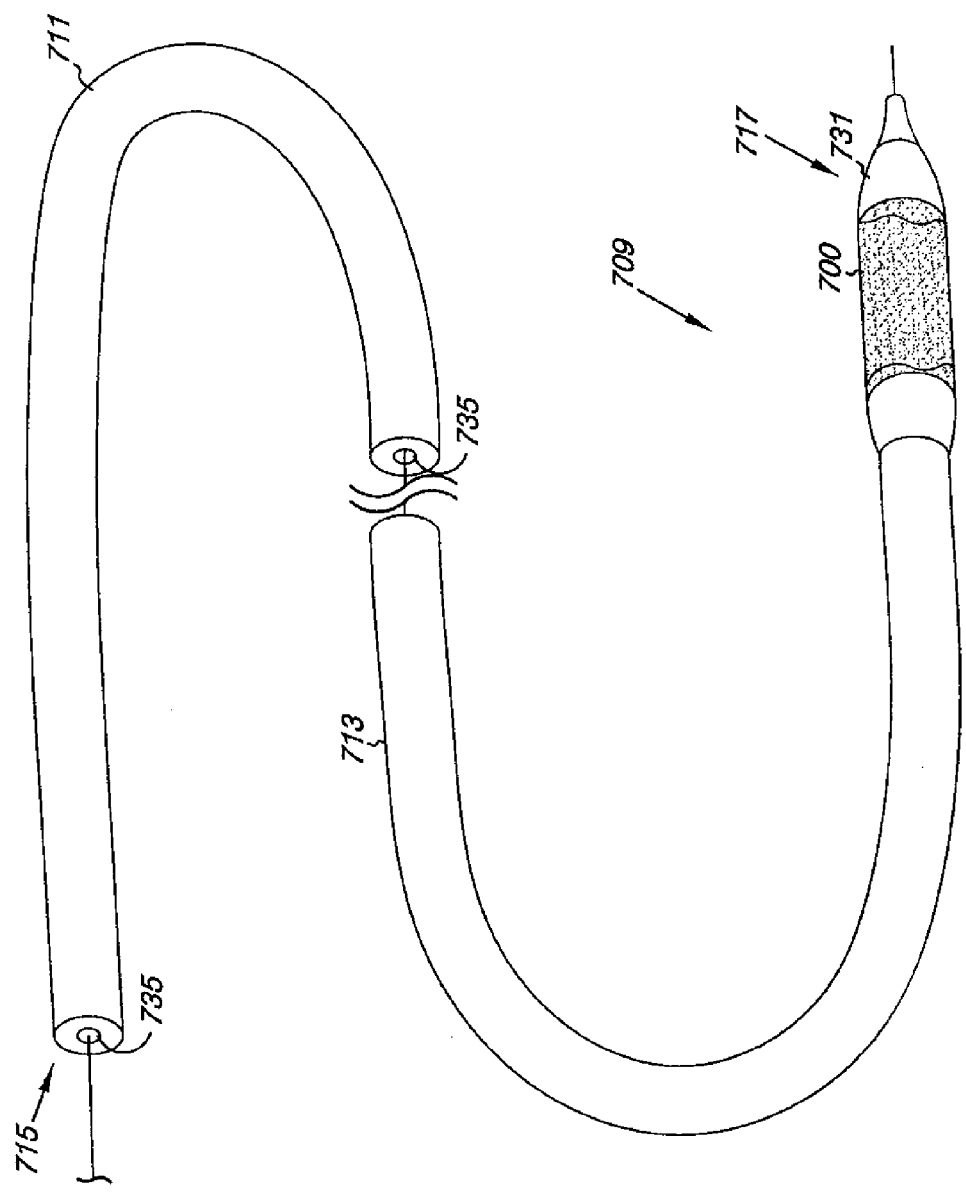
FIG. 7 illustrates an embodiment of a system that includes a valve.

FIG. 7 illustrates an additional embodiment of the system 709. The catheter 711 includes elongate body 713, an inflatable balloon 731 positioned adjacent the distal end 717, and a lumen 735 longitudinally extending in the elongate body 713 of the catheter 711 from the inflatable balloon 731 to the distal end 717. In the present example, the inflatable balloon 731 can be at least partially positioned within the lumen 726 of the valve 700. The inflatable balloon 731 can be inflated through the lumen 735 to deploy the valve 700.

The embodiments of the present invention further include methods for forming the valve of the present invention, as discussed herein. For example, the valve can be formed from the support frame and the cover over at least the outer surface of the support frame, where the cover includes surfaces defining the reversibly sealable opening for unidirectional flow of a liquid through the lumen. In an additional example, the valve can be reversibly joined to the catheter, which can include a process of altering the shape of the valve from a first shape, for example an expanded state, to the compressed state, as described herein.

For example, the valve can be reversibly joined with the catheter by positioning valve in the compressed state at least partially within the sheath of the catheter. In one embodiment, positioning the valve at least partially within the sheath of the catheter includes positioning the valve in the compressed state adjacent the deployment shaft of the catheter. In another embodiment, the sheath of the catheter functions as a retractable sheath, where the valve in the compressed state can be reversibly joined with the catheter by positioning the valve at least partially within the reversible sheath of the catheter. In a further embodiment, the catheter can include an inflatable balloon, where the balloon can be positioned at least partially within the lumen of the valve, for example, in its compressed state.

The embodiments of the valve described herein may be used to replace, supplement, or augment valve structures within one or more lumens of the body. For example, embodiments of the present invention may be used to replace an incompetent cardiac valve of the heart, such as the aortic, pulmonary and/or mitral valves of the heart.

In one embodiment, the method of replacing, supplementing, and/or augmenting a valve structure can include positioning at least part of the catheter including the valve at a predetermined location within an artery of a patient, such as in the aorta adjacent the root of the aortic valve. In positioning the valve of the present invention within the aorta, particular physiological structures need to be taken into consideration. For example, the valve of the present invention works in conjunction with the coronary artery ostia much in the same way as the native aortic valve. This is accomplished due to the configuration of both the support frame and the cover of the valve as described herein.

For example, the configuration of the valve of the present invention permits the valve to be implanted such that the support frame can be positioned between the native aortic valve and the coronary artery ostia. As discussed herein, the open area defined by the support frame allows the valve to be seated adjacent the native aortic valve. In addition, the valve leaflets of the present invention can be in the same relative position as the native valve leaflets. This allows the valve leaflets of the present invention to interact with the coronary ostia positioned in the aortic sinuses (sinuses of Valsalva) adjacent the aortic valve in the similar manner as the native valve leaflets. So, the valve of the present invention can properly accommodate both the aortic valve and the coronary ostia.

In one embodiment, positioning the catheter including the valve within the body lumen includes introducing the catheter into the cardiovascular system of the patient using minimally invasive percutaneous, transluminal catheter based delivery system, as is known in the art. For example, a guidewire can be positioned within the cardiovascular system of a patient that includes the predetermined location. The catheter, including valve, as described herein, can be positioned over the guidewire and the catheter advanced so as to position the valve at or adjacent the predetermined location. In one embodiment, radiopaque markers on the catheter and/or the valve, as described herein, can be used to help locate and position the valve.

The valve can be deployed from the catheter at the predetermined location in any number of ways, as described herein. In one embodiment, valve of the present invention can be deployed and placed in any number of cardiovascular locations. For example, valve can be deployed and placed within a major artery of a patient. In one embodiment, major arteries include, but are not limited to, the aorta. In addition, valves of the present invention can be deployed and placed within other major arteries of the heart and/or within the heart itself, such as in the pulmonary artery for replacement and/or augmentation of the pulmonary valve and between the left atrium and the left ventricle for replacement and/or augmentation of the mitral valve. Other locations are also possible.

As discussed herein, the valve can be deployed from the catheter in any number of ways. For example, the catheter can include the retractable sheath in which valve can be at least partially housed, as discussed herein. Valve can be deployed by retracting the retractable sheath of the catheter, where the valve self-expands to be positioned at the predetermined location. In an additional example, the catheter can include a deployment shaft and sheath in which valve can be at least partially housed adjacent the deployment shaft, as discussed herein. Valve can be deployed by moving the deployment shaft through the catheter to deploy valve from the sheath, where the valve self-expands to be positioned at the predetermined location. In an additional embodiment, the valve can be deployed through the use of an inflatable balloon. In a further embodiment, the valve can partially self-expand upon retracting a sheath in which the valve is located, and then deployed through the use of an inflatable balloon.

Once implanted, the valve can provide sufficient contact and expansion force against the body lumen wall to prevent retrograde flow between the valve and the body lumen wall, and to securely located the valve and prevent migration of the valve. For example, the valve can be selected to have a larger expansion diameter than the diameter of the inner wall of the body lumen. This can then allow valve to exert a force on the body lumen wall and accommodate changes in the body lumen diameter, while maintaining the proper placement of valve. As described herein, the valve can engage the lumen so as to reduce the volume of retrograde flow through and around valve. It is, however, understood that some leaking or fluid flow may occur between the valve and the body lumen and/or through valve leaflets.

While the present invention has been shown and described in detail above, it will be clear to the person skilled in the art that changes and modifications may be made without departing from the spirit and scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the support frame 102 and/or the cover 104 can be coated with a non-thrombogenic biocompatible material, as are known or will be known. Other biologically active agents or cells may also be utilized.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A system, comprising:
 a cardiac valve, where the cardiac valve includes:
  a support frame having a first end member and a second end member separated from the first end member by a number of cross members that define a lumen;
  a cover at the second end member to form a first valve leaflet and a second valve leaflet, where a portion of the first valve leaflet and the second valve leaflet join to form a reversibly sealable opening for unidirectional flow of a liquid through the cardiac valve; and
  a tubular member of the cardiac valve, coupled to the cardiac valve, and having a predetermined length extending from and in fluid tight communication with the cover, where the tubular member includes a first end on a first side of the first and second valve leaflets and a second end on a second side of the first and second valve leaflets opposite the first side to allow for fluid communication across the valve when the first and second valve leaflets are in a closed position and where the first end and the second end of the tubular member are positionable within and stay within a patient's body after removal of a delivery catheter and where the tubular member includes a predetermined bend between the first end and the second end; and
 a catheter including a proximal end and a distal end, the cardiac valve located between the proximal end and distal end of the catheter.

2. The system of claim 1, where the catheter includes an elongate body having a lumen longitudinally extending to the distal end, a deployment shaft positioned within the lumen, and a sheath positioned adjacent the distal end, the cardiac valve positioned at least partially within the sheath and adjacent the deployment shaft, where the deployment shaft moves within the lumen to deploy the cardiac valve.

3. The system of claim 1, where the catheter includes an elongate body and a retractable sheath over at least a portion of the elongate body, the cardiac valve positioned at least partially within the retractable sheath, where the retractable sheath moves along the elongate body to deploy the cardiac valve.

4. The system of claim 1, where the catheter includes an inflatable balloon positioned adjacent the distal end and a lumen longitudinally extending in an elongate body of the catheter from the inflatable balloon to the distal end, the inflatable balloon at least partially positioned within the lumen of the cardiac valve, where the inflatable balloon inflates to deploy the cardiac valve.

5. The system of claim 1, where the second end member includes a first convex curve and a second convex curve; and the cover extends between the first convex curve and the second convex curve to form the first valve leaflet and the second valve leaflet of a bi-leaflet cardiac valve.

6. The system of claim 5, where the cover extends over an outer surface of the support frame to form the bi-leaflet cardiac valve.

7. The system of claim 6, where the cover extends over both an inner surface and the outer surface of the support frame to form the bi-leaflet cardiac valve.

8. The cardiac valve of claim 1, where the cover extends between convex curves of the second end member to form a first valve leaflet, a second valve leaflet, and a third valve leaflet of a tri-leaflet cardiac valve; and where a portion of the first valve leaflet, the second valve leaflet and the third valve leaflet join to form the reversibly sealable opening for unidirectional flow of the liquid through the cardiac valve.

9. The system of claim 1, where the first end member defines an open area between a sequence of convex curves and concave curves of the first end member.

10. The system of claim 1, where the cover further includes a surface defining an opening, where the tubular member extends from and is in fluid tight communication with the opening.

* * * * *